(12) United States Patent
Burgoon, Jr. et al.

(10) Patent No.: US 7,855,291 B2
(45) Date of Patent: *Dec. 21, 2010

(54) PROCESS FOR THE PREPARATION OF SUBSTITUTED PHENYLALANINES

(75) Inventors: Hugh Alfred Burgoon, Jr., Hamilton, NJ (US); Ramanaiah C. Kanamarlapudi, Bridgewater, NJ (US); Iain Fraser Pickersgill, Newtown, PA (US); Zhi-Cai Shi, Monmouth Junction, NJ (US); Wenxue Wu, Princeton Junction, NJ (US); Haiming Zhang, Lawrenceville, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 836 days.

This patent is subject to a terminal disclaimer.

(21) Appl. No.: 11/647,517

(22) Filed: Dec. 28, 2006

(65) Prior Publication Data

US 2009/0048280 A1 Feb. 19, 2009

Related U.S. Application Data

(60) Provisional application No. 60/754,785, filed on Dec. 29, 2005.

(51) Int. Cl.
*C07D 239/34* (2006.01)
*C07D 403/12* (2006.01)
*A61K 31/506* (2006.01)
*A61K 31/505* (2006.01)
*A61P 9/02* (2006.01)

(52) U.S. Cl. ............ 544/320; 544/334; 544/335; 514/269

(58) Field of Classification Search ............ 544/320, 544/334, 335
See application file for complete search history.

(56) References Cited

U.S. PATENT DOCUMENTS

| | | | |
|---|---|---|---|
| 4,866,181 A | 9/1989 | Brown | |
| 4,916,074 A | 4/1990 | Yoshida | |
| 5,233,111 A | 8/1993 | Notte | |
| 5,859,020 A | 1/1999 | Preuss | |
| 6,916,933 B2 | 7/2005 | Kaplan | |
| 7,553,840 B2 * | 6/2009 | Devasagayaraj et al. | .... 514/269 |
| 2003/0144541 A1 | 7/2003 | Jacquot | |
| 2005/0096353 A1 | 5/2005 | Ackermann | |
| 2005/0282900 A1 | 12/2005 | Kawaguchi | |
| 2006/0128956 A1 | 6/2006 | Hocek | |
| 2006/0148862 A1 | 7/2006 | Clary | |
| 2007/0191370 A1 * | 8/2007 | Devasagayaraj et al. | .... 514/241 |
| 2009/0088447 A1 | 4/2009 | Bednarz | |
| 2009/0099206 A1 | 4/2009 | Iimura | |

FOREIGN PATENT DOCUMENTS

| WO | WO 03/104189 | 12/2003 |
|---|---|---|
| WO | WO 03/104200 | 12/2003 |

OTHER PUBLICATIONS

Dondoni, A., et al., *Organic Let.* 6(17):2929-2932 (2004).
Firooznia et al., *Tetrahedron Lett.*, 49:213-216 (1999).
Hutton, C.A., and Skaff, O., *Tetrahedron Let.* 44(26):4895-4898 (2003).
Kuijpers, B.H.M., et al., *Organic Let.* 6(18):3123-3126 (2004).
Moussebois, C., et al., *Helv. Chimica Acta* 60(1):237-242 (1977).
Peyman, A., et al., *Angew. Chemie* 39(16):2874-2877 (2000).
Yoburn, J.C. and Van Vranken, D.L., *Organic Let.* 5(16):2817-2820 (2003).
Shi, Z. et al., *J. Med. Chem.* 51(13):3684-3687 (2008).
International Search Report issued for corresponding international patent application PCT/US2008/081054, Jun. 7, 2009.

* cited by examiner

*Primary Examiner*—Venkataraman Balasubramanian
(74) *Attorney, Agent, or Firm*—Max Bachrach

(57) ABSTRACT

Intermediates and synthetic processes for the preparation of substituted phenylalanine-based compounds (e.g., of Formula I) are disclosed:

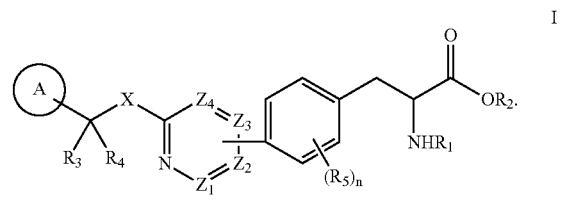

10 Claims, No Drawings

PROCESS FOR THE PREPARATION OF SUBSTITUTED PHENYLALANINES

This application claims priority to U.S. provisional application No. 60/754,785, filed Dec. 29, 2005, the entirety of which is incorporated herein by reference.

1. FIELD OF THE INVENTION

This invention relates to synthetic processes used to make substituted phenylalanine-based compounds.

2. BACKGROUND

The neurotransmitter serotonin [5-hydroxytryptamine (5-HT)] is involved in multiple central nervous facets of mood control and in regulating sleep, anxiety, alcoholism, drug abuse, food intake, and sexual behavior. In peripheral tissues, serotonin is reportedly implicated in the regulation of vascular tone, gut motility, primary hemostasis, and cell-mediated immune responses. Walther, D. J., et al., *Science* 299:76 (2003).

The enzyme tryptophan hydroxylase (TPH) catalyzes the rate limiting step of the biosynthesis of serotonin. Two isoforms of TPH have been reported: TPH1, which is expressed in the periphery, primarily in the gastrointestinal (GI) tract, and; TPH2, which is expressed in the brain. Id. The isoform TPH1 is encoded by the tph1 gene; TPH2 is encoded by the tph2 gene. Id.

Mice genetically deficient for the tph1 gene ("knockout mice") have been reported. In one case, the mice reportedly expressed normal amounts of serotonin in classical serotonergic brain regions, but largely lacked serotonin in the periphery. Id. In another, the knockout mice exhibited abnormal cardiac activity, which was attributed to a lack of peripheral serotonin. Côté, F., et al., *PNAS* 100(23):13525-13530 (2003).

Because serotonin is involved in so many biochemical processes, drugs that affect serotonin levels are often attended by adverse effects. Thus, a need exists for new methods of affecting serotonin levels.

3. SUMMARY OF THE INVENTION

This invention encompasses the preparation of compounds of formula I:

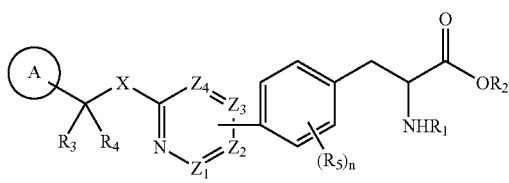

I and pharmaceutically acceptable salts and solvates thereof, wherein the various substituents are defined herein. When administered to mammals, preferred compounds of this formula inhibit TPH (e.g., TPH1), and may be useful in the treatment of various diseases and disorders.

This invention is also directed to various intermediates that are useful in the synthesis of compounds of formula I.

4. DETAILED DESCRIPTION

This invention is based on the discovery of a novel process that can be used to efficiently prepare compounds of formula I. When administered to mammals, preferred compounds of formula I inhibit peripheral TPH, and may be used in the treatment of various diseases and disorders, including disorders of the GI tract. See generally, U.S. patent application No. 60/754,955, filed Dec. 29, 2005.

4.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., *Protective Groups in Organic Synthesis* ($3^{rd}$ ed., John Wiley & Sons: 1999); Larock, R. C., *Comprehensive Organic Transformations* ($2^{nd}$ ed., John Wiley & Sons: 1999).

Unless otherwise indicated, the term "pseudohalogen" refers to a polyatomic anion that resembles a halide ion in its acid-base, substitution, and redox chemistry, generally has low basicity, and forms a free radical under atom transfer radical polymerization conditions. Examples of pseudohalogens include azide ions, cyanide, cyanate, thiocyanate, thiosulfate, sulfonates, and sulfonyl halides.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

4.2. Methods of Synthesis

This invention encompasses the preparation of compounds of formula I:

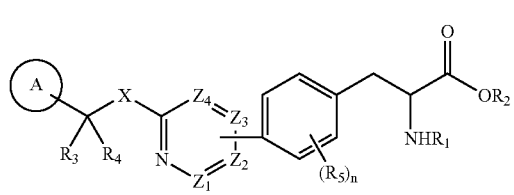

I and pharmaceutically acceptable salts and solvates thereof, wherein the various substituents are defined herein. The invention is particularly directed to the synthesis of compounds of formulae I(b), I(c), I(d) and I(e):

I(b)

I(c)

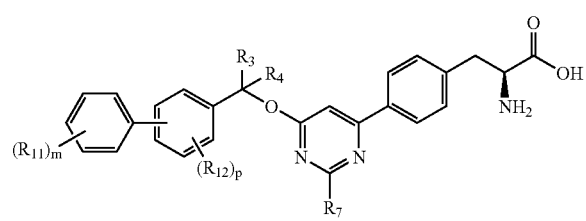

-continued

I(d)

I(e)

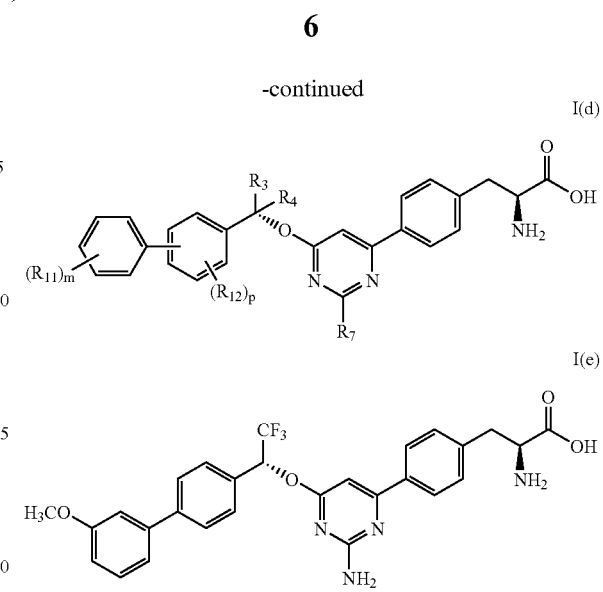

In one aspect of the invention, the synthesis of such compounds is achieved via a compound of formula I(a):

I(a)

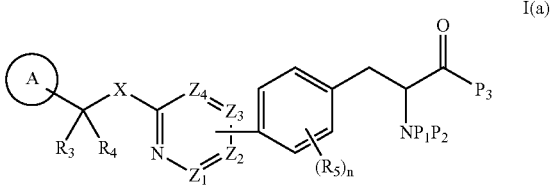

One embodiment of the invention encompasses a method of preparing a compound of formula I(a), which comprises contacting a compound of formula II:

II

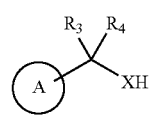

with a compound of formula III:

III

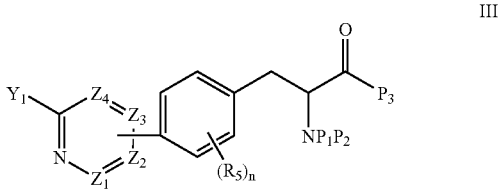

under conditions sufficient for the formation of the compound of formula I(a), wherein:

A is optionally substituted cycloalkyl, aryl, or heterocycle;

X is O, S, or $NR_6$;

$Y_1$ is halogen or pseudohalogen;

one of $Z_1$, $Z_2$, $Z_3$, and $Z_4$ is a carbon atom attached to the adjacent optionally substituted phenyl moiety, and the others are each independently $CR_7$ or N;

$P_1$ is $R_1$ or a protecting group;

$P_2$ is a protecting group;

$P_3$ is $OR_2$, $SR_2$, $NR_9R_{10}$, $NHNHR_9$, or a protecting group;

$R_1$ is hydrogen or optionally substituted alkyl, alkyl-aryl, alkyl-heterocycle, aryl, or heterocycle;

$R_2$ is hydrogen or optionally substituted alkyl, alkyl-aryl, alkyl-heterocycle, aryl, or heterocycle;

$R_3$ is hydrogen, cyano, or optionally substituted alkyl or aryl;

$R_4$ is hydrogen, cyano, or optionally substituted alkyl or aryl;

each $R_5$ is independently hydrogen, cyano, nitro, halogen, $OR_8$, $NR_9R_{10}$, or optionally substituted alkyl, alkyl-aryl or alkyl-heterocycle;

$R_6$ is hydrogen or optionally substituted alkyl or aryl;

each $R_7$ is independently hydrogen, cyano, nitro, halogen, $OR_8$, $NR_9R_{10}$, or optionally substituted alkyl, alkyl-aryl or alkyl-heterocycle;

each $R_8$ is independently hydrogen or optionally substituted alkyl, alkyl-aryl or alkyl-heterocycle;

each $R_9$ is independently hydrogen, a protecting group, or optionally substituted alkyl, alkyl-aryl or alkyl-heterocycle;

each $R_{10}$ is independently hydrogen, a protecting group, or optionally substituted alkyl, alkyl-aryl or alkyl-heterocycle; and n is 1-4.

In one embodiment, $P_3$ is $OR_2$. In another, $R_2$ is hydrogen. In another, $Z_1$ is $CR_7$. In another, $R_7$ is $NR_9R_{10}$. In another, $R_9$ is hydrogen. In another, $R_{10}$ is hydrogen. In another, $Z_2$ is N. In another, $Z_3$ is a carbon atom attached to the adjacent optionally substituted phenyl moiety. In another, $Z_4$ is $CR_7$. In another, $R_7$ is hydrogen. In another, n is 1. In another, $R_5$ is hydrogen. In another, X is O. In another, $R_3$ is hydrogen. In another, $R_4$ is optionally substituted alkyl. In another, $R_4$ is —$CF_3$. In another, A is optionally substituted biphenyl.

In a particular embodiment, the compound of formula II is of formula II(a):

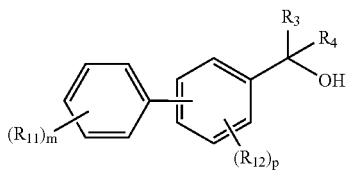

II(a)

wherein: $R_{11}$ is independently hydrogen, cyano, nitro, halogen, $OR_8$, $NR_9R_{10}$, or optionally substituted alkyl, alkyl-aryl or alkyl-heterocycle; each $R_{12}$ is independently hydrogen, cyano, nitro, halogen, $OR_8$, $NR_9R_{10}$, or optionally substituted alkyl, alkyl-aryl or alkyl-heterocycle; m is 1-5; and p is 1-4. In another, the compound of formula II(a) is of formula II(b):

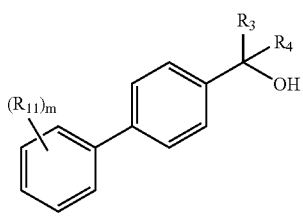

II(b)

In another embodiment, the compound of formula III is of formula III(a):

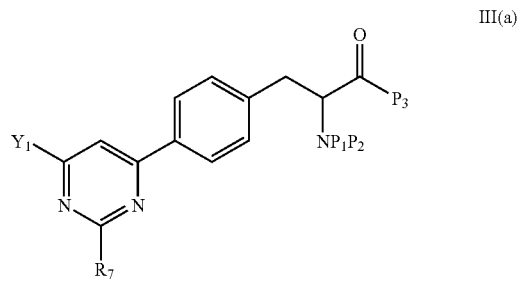

III(a)

In another, the compound of formula III(a) is of formula III(b):

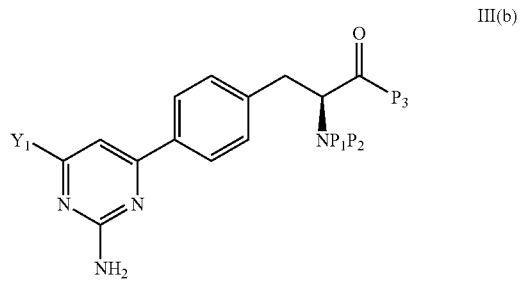

III(b)

In a particular embodiment, the compound of formula II is prepared by contacting a compound of formula IV:

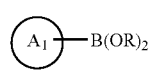

IV with a compound of formula V:

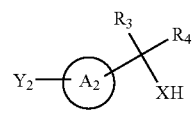

V under conditions sufficient for the formation of the compound of formula II, wherein: $A_1$ is optionally substituted cycloalkyl, aryl, or heterocycle; $A_2$ is optionally substituted cycloalkyl, aryl, or heterocycle; $Y_2$ is halogen or pseudohalogen; and each R is independently hydrogen, optionally substituted alkyl, alkyl-aryl, alkyl-heterocycle, aryl, or heterocycle, or are taken together with the oxygen atoms to which they are attached to provide a cyclic dioxaborolane.

In one embodiment, $A_1$ is optionally substituted phenyl. In another, $A_1$ is anisole. In another, $A_2$ is optionally substituted phenyl. In another, $A_2$ is phenyl. In another, $R_3$ is hydrogen. In another, $R_4$ is optionally substituted alkyl. In another, $R_4$ is —$CF_3$. In another, X is O.

In a particular embodiment, the compound of formula IV is of formula IV(a):

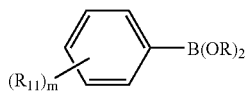

IV(a)

wherein: each $R_{11}$ is independently hydrogen, cyano, nitro, halogen, $OR_8$, $NR_9R_{10}$, or optionally substituted alkyl, alkyl-aryl or alkyl-heterocycle; and m is 1-5. In another, the compound of formula IV(a) is of formula IV(b):

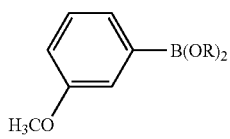

IV(b)

In another, the compound of formula V is of formula V(a):

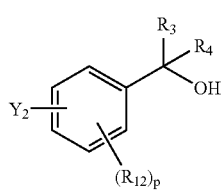

V(a)

wherein: each $R_{12}$ is independently hydrogen, cyano, nitro, halogen, $OR_8$, $NR_9R_{10}$, or optionally substituted alkyl, alkyl-aryl or alkyl-heterocycle; and p is 1-4. In one embodiment, the compound of formula V(a) is of formula V(b):

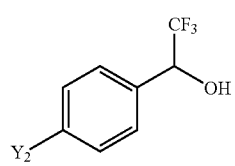

V(b)

In a particular embodiment, the compound of formula III (a) is prepared by contacting a compound of formula VI:

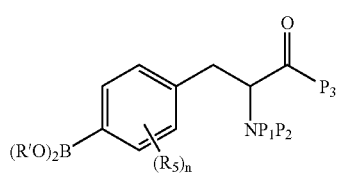

VI with a compound of formula VII:

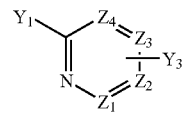

VII under conditions sufficient for the formation of the compound of formula III, wherein: $Y_3$ is halogen or pseudohalogen; and each R' is independently hydrogen or optionally substituted alkyl, alkyl-aryl, alkyl-heterocycle, aryl, or heterocycle, or are taken together with the oxygen atoms to which they are attached to provide a cyclic dioxaborolane.

In one embodiment, n is 1. In another, $R_5$ is hydrogen. In another, $Z_1$ is $CR_7$. In another, $R_7$ is $NR_9R_{10}$. In another, $R_9$ is hydrogen. In another, $R_{10}$ is hydrogen. In another, $Z_2$ is N. In another, $Z_3$ is a carbon atom attached to the adjacent optionally substituted phenyl moiety. In another, $Z_4$ is $CR_7$. In another, $R_7$ is hydrogen.

In a particular embodiment, the compound of formula VI is of formula VI(a):

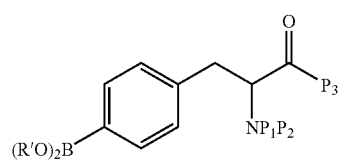

VI(a)

In another, the compound of formula VI(a) is of formula VI(b):

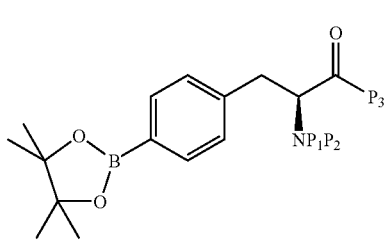

VI(b)

In another, the compound of formula VI(a) is of formula VI(c):

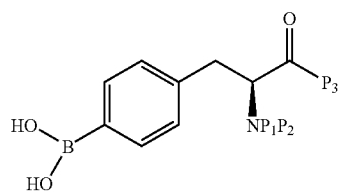

VI(c)

In another, the compound of formula VII is of formula VII(a):

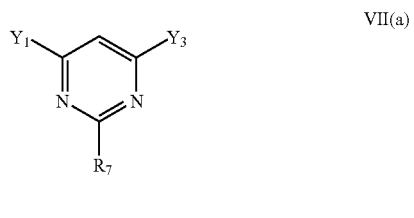

In another, the compound of formula VII(a) is of formula VII(b):

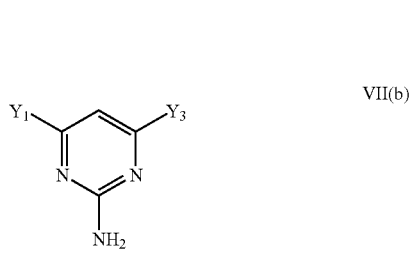

One embodiment of the invention comprises deprotecting the compound of formula I(a) to provide a compound of formula I:

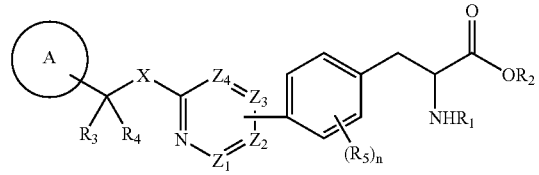

wherein: $R_1$ is hydrogen or optionally substituted alkyl, alkyl-aryl, alkyl-heterocycle, aryl, or heterocycle. In a particular embodiment, the compound of formula I is of formula I(b):

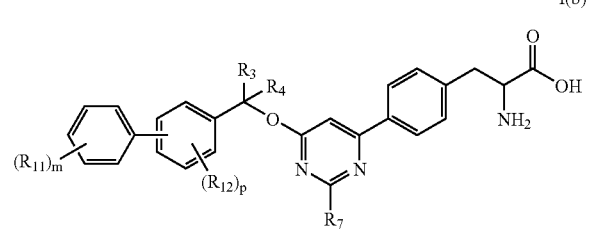

wherein: each $R_{11}$ is independently hydrogen, cyano, nitro, halogen, $OR_8$, $NR_9R_{10}$, or optionally substituted alkyl, alkyl-aryl or alkyl-heterocycle; each $R_{12}$ is independently hydrogen, cyano, nitro, halogen, $OR_8$, $NR_9R_{10}$, or optionally substituted alkyl, alkyl-aryl or alkyl-heterocycle; m is 1-5; and p is 1-4.

In one embodiment, the compound of formula I(b) is of formula I(c), I(d) or I(e):

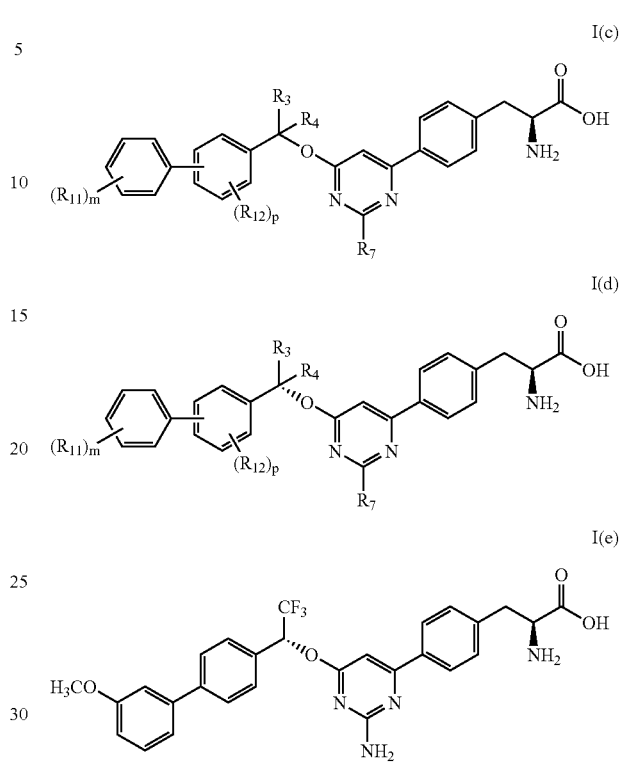

Certain embodiments of the invention can be understood with reference to Scheme 1:

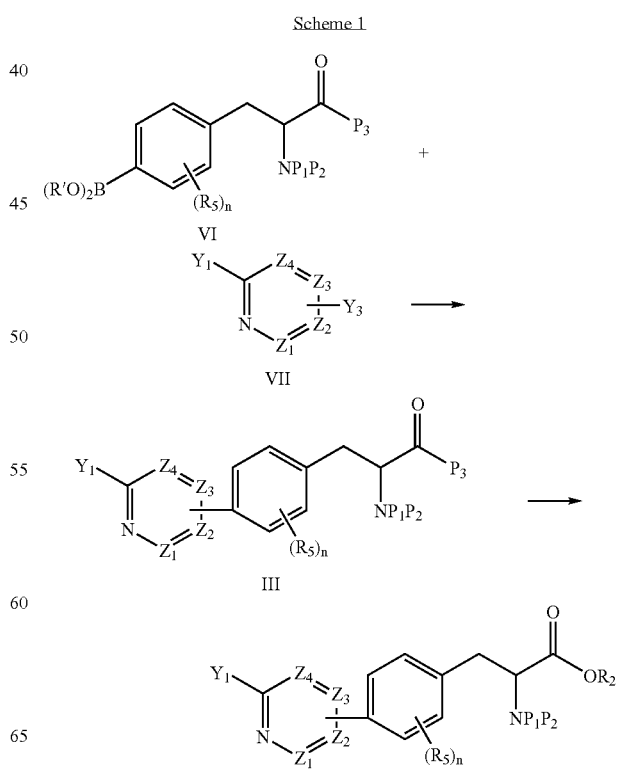

-continued

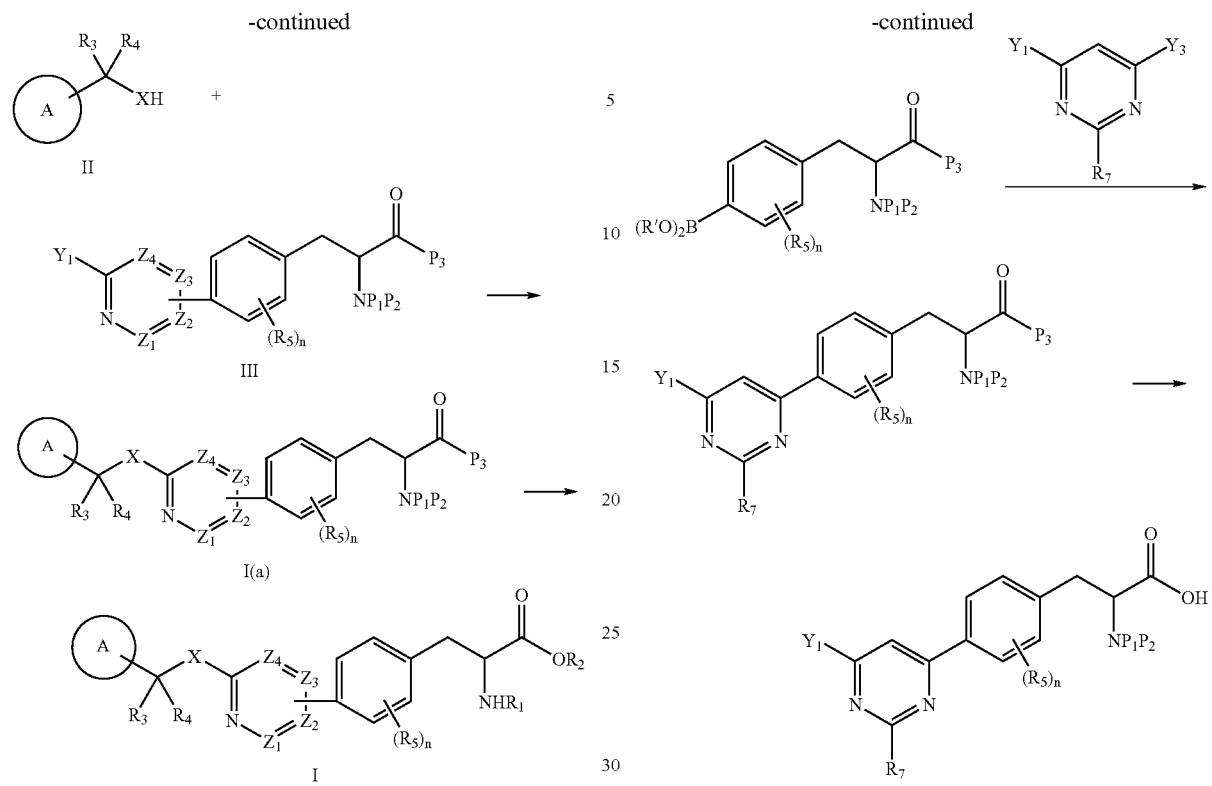

In this approach, compounds of general formulae VI and VII are coupled under conditions suitable for the formation of a compound of formula III (e.g., contact with a transition metal catalyst, a base, and a solvent or solvent mixture with water), moieties of which may be deprotected if appropriate. The compound of formula III is then coupled with a compound of formula II under conditions sufficient to provide a compound of formula I(a) (e.g., nucleophilic substitution conditions), which is deprotected (e.g., by hydrolysis under acidic or basic conditions) to afford the compound of general formula I.

A more specific adaptation of the approach shown in Scheme 1 is provided below. Scheme 2(a) shows the preparation of two intermediate compounds:

Conditions sufficient for the formation of the compound of formula II(a) include the use of a transition metal catalyst, a base, and a solvent or solvent mixture with water. The intermediate compounds are coupled as shown below in Scheme 2(b), to provide a compound that is deprotected to provide the final product:

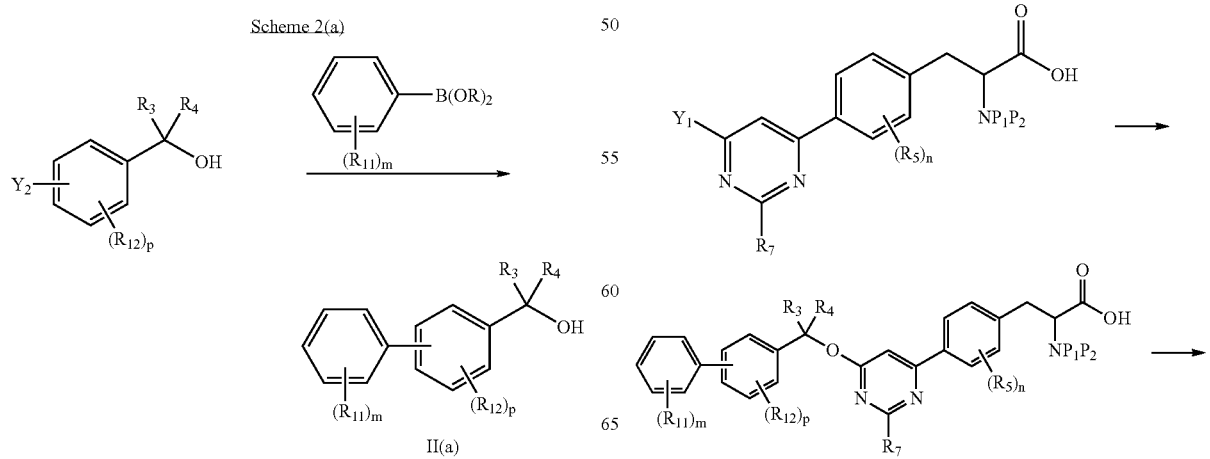

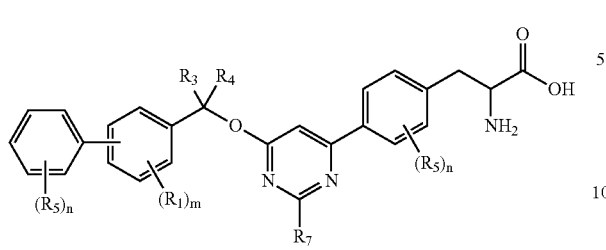

Various reaction conditions may be used in this approach to obtain the desired product. As those skilled in the art will immediately recognize, preferred reaction conditions may depend on the specific compounds involved. In one embodiment of the invention, $Y_1$ is Cl. In another, $Y_2$ is Br. In another, $Y_3$ is Cl. In another, R is hydrogen. In another, R' is hydrogen. In another, both R' are taken together with the oxygen atoms to which they are attached to provide 4,4,5,5-tetramethyl-1,3,2-dioxaborolan-2-yl.

In another embodiment, each protecting group is independently aryl-alkyl, heteroaryl-alkyl, or —C(O)$R_{13}$, wherein $R_{13}$ is alkyl, aryl-alkyl, aryl, heterocycle, alkoxy, aryloxy, or aryl-alkoxy. Examples of protecting groups include benzyl, diphenylmethyl, trityl, Cbz, Boc, Fmoc, methoxycarbonyl, ethoxycarbonyl, and pthalimido.

In addition to the various synthetic methods disclosed herein, this invention encompasses novel compounds that can be used to prepare compounds of formula I.

Examples include compounds of the formula:

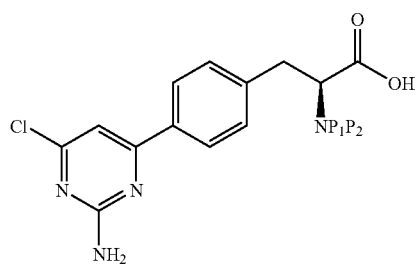

and salts and solvates thereof, wherein: $P_1$ is $R_1$, —C(O)$R_{13}$, or optionally substituted alkyl, alkyl-aryl, alkyl-heterocycle, aryl, or heterocycle; $P_2$ is —C(O)$R_{13}$ or optionally substituted alkyl, alkyl-aryl, alkyl-heterocycle, aryl, or heterocycle; $R_1$ is hydrogen or optionally substituted alkyl, alkyl-aryl, alkyl-heterocycle, aryl, or heterocycle; and each $R_{13}$ is independently alkyl, aryl-alkyl, aryl, heterocycle, alkoxy, aryloxy, or aryl-alkoxy.

In one embodiment, $P_1$ is hydrogen. In another, $P_2$ is benzyl, diphenylmethyl, trityl, Cbz, Boc, Fmoc, methoxycarbonyl, ethoxycarbonyl, or pthalimido. A particular compound is of the formula:

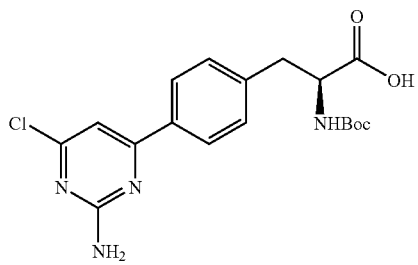

The invention also encompasses compounds of the formula:

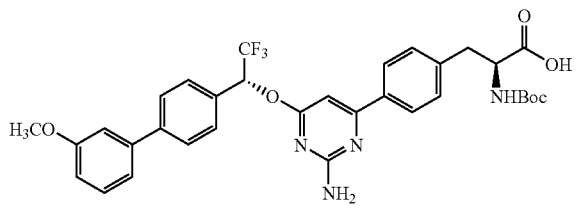

and salts and solvates thereof, wherein $P_1$ is $R_1$, —C(O)$R_{13}$, or optionally substituted alkyl, alkyl-aryl, alkyl-heterocycle, aryl, or heterocycle; $P_2$ is —C(O)$R_{13}$ or optionally substituted alkyl, alkyl-aryl, alkyl-heterocycle, aryl, or heterocycle; $R_1$ is hydrogen or optionally substituted alkyl, alkyl-aryl, alkyl-heterocycle, aryl, or heterocycle; and each $R_{13}$ is independently alkyl, aryl-alkyl, aryl, heterocycle, alkoxy, aryloxy, or aryl-alkoxy.

In one embodiment, $P_1$ is hydrogen. In another, $P_2$ is benzyl, diphenylmethyl, trityl, Cbz, Boc, Fmoc, methoxycarbonyl, ethoxycarbonyl, or pthalimido. A particular compound is of the formula:

This invention also encompasses compounds of the formula:

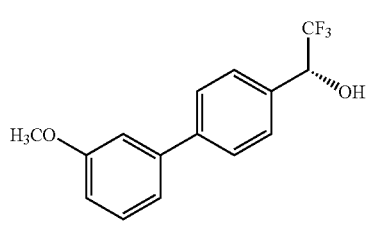

and salts and solvates thereof.

5. EXAMPLES
The following non-limiting examples describe the synthesis of (S)-2-amino-3-(4-(2-amino-6-((R)-2,2,2-trifluoro-1-(3'-methoxybiphenyl-4-yl)ethoxy)pyrimidin-4-yl)phenyl)-propanoic acid.
Generally, intermediate compounds 3 and 8 are first prepared, as shown below in Schemes 3(a) and (b):
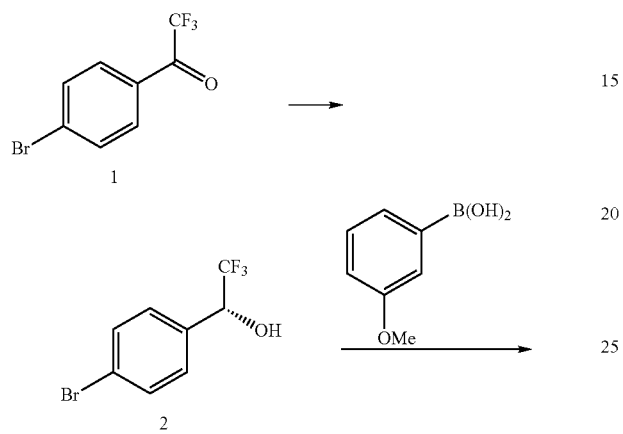
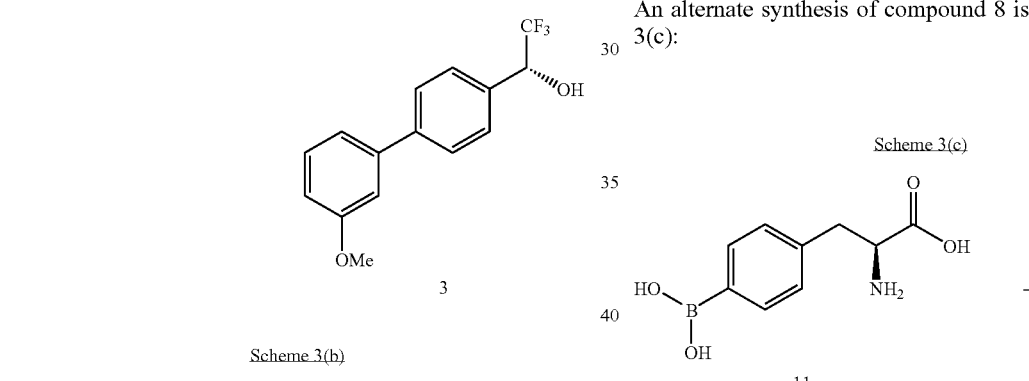
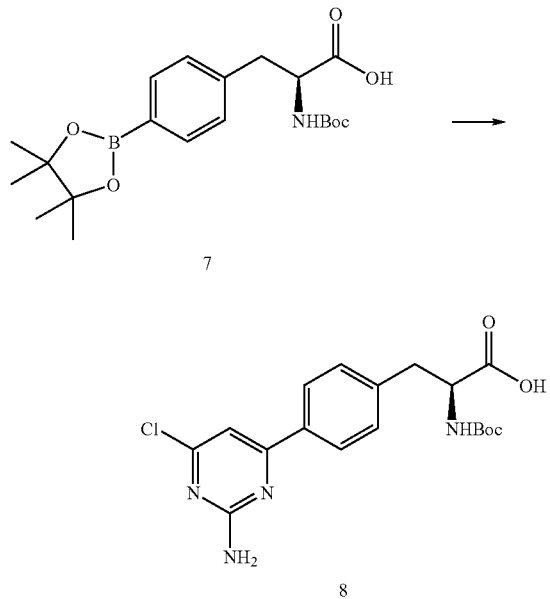
An alternate synthesis of compound 8 is shown in Scheme 3(c):
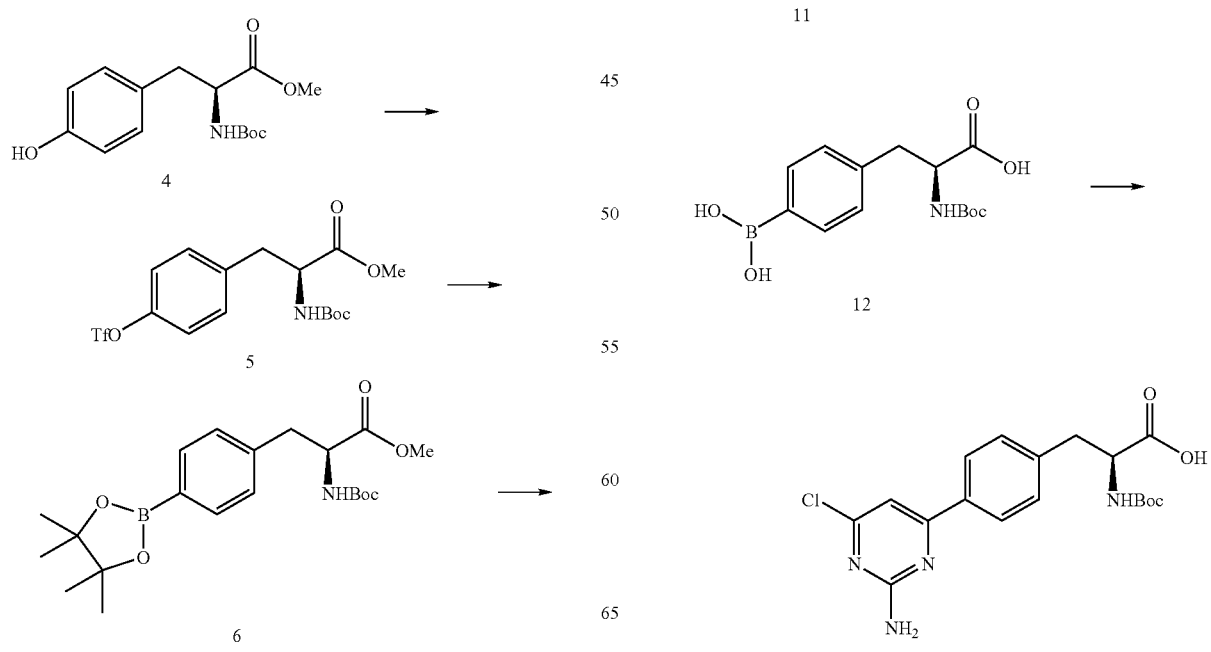

The intermediates are then coupled as shown below in Scheme 3(d):

Scheme 3(d)

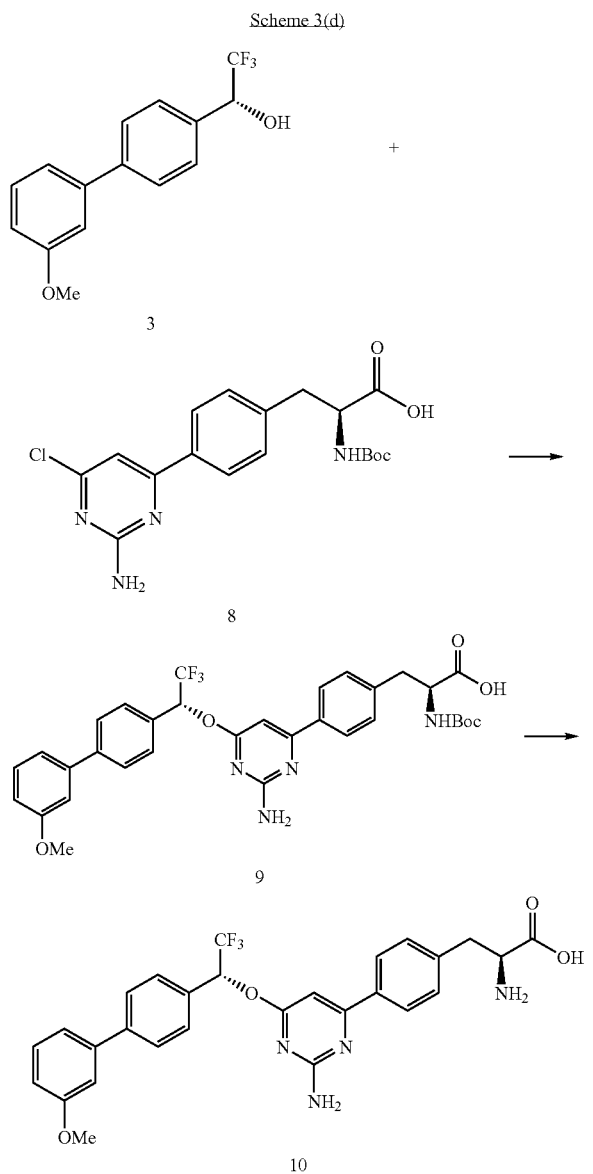

In the following examples, yields of various reactions are reported on a molar basis. Unless otherwise indicated, reagents are commercially available and may be purchased from Sigma-Aldrich Company, Inc. (Milwaukee, Wis., USA).

5.1. Preparation of (R)-1-(4-Bromophenyl)-2,2,2-trifluoroethanol (2)

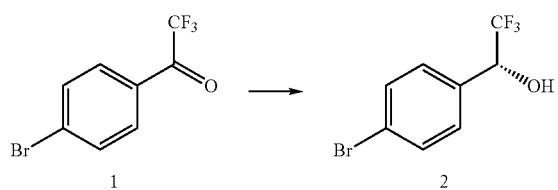

This compound was prepared based on a literature procedure (Ohkuma, et al. *J. Am. Chem. Soc.*, 1998, 120, 13529-13530). To a 1 L high pressure vessel was charged 4-bromotrifluoroacetophenone (1, Wilmington PharmaTech, Delaware, 100.0 g, 395 mmol), potassium tert-butoxide (1 M solution in 2-methyl-2-propanol, 5.0 ml, 10.0 mmol, 0.025 eq), and catalyst [(trans)-RuCl$_2$[(R)-Xyl-P-Phos][(R)-DIAPEN] (Johnson Matthey, New Jersey, 200 mg, 0.16 mmol, 0.04% mol). The mixture was dissolved in anhydrous 2-propanol (175 ml) and the entire vessel was purged with argon by 3 vacuum-thaw cycles. The reaction mixture was then purged with hydrogen by 3 vacuum-thaw cycles. The reaction was carried out under 60 psi hydrogen atmosphere. After 24 h of stirring and no more hydrogen consumption, the reaction was deemed complete by GC-MS analysis (no more starting ketone). The contents of the reaction vessel were transferred to a round bottom flask with MeOH rinsing (3×20 ml), and concentrated under reduced pressure until no more solvent was distilling off. The resulting orange-brown oil was then dissolved in heptane (1000 ml) and washed with water (2×100 ml), brine (100 ml) and dried over sodium sulfate. To the dried organic layer was added Darco® activated charcoal (20 g) and Hyflo® Super Cel (20 g) and the mixture was heated at 70° C. for 1 h. The mixture was filtered hot to give a light yellow solution. The filtrate was concentrated under reduced pressure with heating (~50-60° C.) until no more solvent was distilling. The resulting yellow oil was dissolved in 60° C. warm heptane (350 ml) and allowed to stir while cooling. As the temperature cooled to rt., white solid began to precipitate. After 4 h of stirring, the solids were filtered and dried to give the titled product (63.5 g, 63%, >99% ee) as a white powder. m.p.: 56.7° C. [α]=−30.1 (c1.09, ethanol). GC-MS (CI): MH$^+$=255.8. $^1$H NMR (CDCl$_3$) δ 7.58 (m, 2H), 7.42 (d, J=8.3 Hz, 2H), 5.00 (m, 1H), 2.62 (d, J=4.3 Hz, 1H). $^{13}$CNMR (CDCl$_3$): δ 133.2, 132.2, 129.5, 125.7, 124.3 (q, J=282 Hz), 72.6 (q, J=32 Hz). $^{19}$F NMR (CDCl$_3$): δ-78.5 (d, J=5.6 Hz).

5.2. (S)-1-(4-Bromophenyl)-2,2,2-trifluoroethanol

Using a procedure similar to the above example, the titled compound was prepared using catalyst [(trans)-RuCl$_2$[(S)-Xyl-P-Phos][(S)-DIAPEN] (Johnson Matthey, New Jersey).

5.3. (R)-2,2,2-Trifluoro-1-(p-tolyl)ethanol

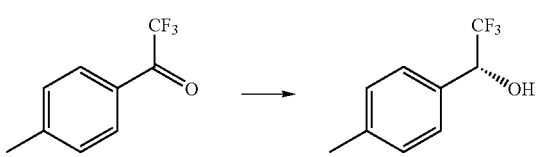

Similarly, 2,2,2-trifluoro-1-(p-tolyl)ethanone was hydrogenated using catalyst [(trans)-RuCl$_2$[(R)-Xyl-P-Phos][(R)-DIAPEN] to give the titled compound. m.p.: 44.2° C.

$^1$H NMR (CDCl$_3$): δ 7.38 (d, J=6.0 Hz, 2H), 7.25 (d, J=6.0 Hz, 2H), 5.00 (dq, J$_1$=6.6 Hz, J$_2$=3.3 Hz, 1H), 2.49 (d, J=3.8 Hz, 1H), 2.42 (s, 3H).

5.4. (S)-2,2,2-Trifluoro-1-(p-tolyl)ethanol

Similarly, the titled compound was prepared using catalyst [(trans)-RuCl$_2$[(S)-Xyl-P-Phos][(S)-DIAPEN].

5.5. (R)-2,2,2-Trifluoro-1-(3'-methoxybiphenyl-4-yl)ethanol (3)

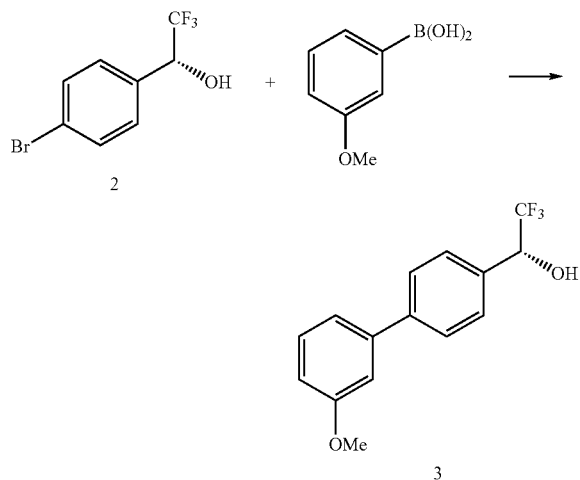

To a stirred solution of (R)-1-(4-bromophenyl)-2,2,2-trifluoroethanol (2, 69 g, 0.27 mol, >99% ee), 3-methoxy phenylboronic acid (Matrix, 51 g, 0.34 mol, 97% purity), and bis(triphenylphosphine)palladium(II) dichloride (0.95 g, 0.5% mol) in ethanol (560 ml) was added a solution of potassium carbonate (112 g, 0.81 mol) in water (140 ml) under nitrogen. The resulting mixture was heated at 75° C. for 1 h and deemed complete by GC-MS or TLC. After reaction mixture was cooled to 40° C., it was filtered through a pad of Celite, washed with methanol (3×100 ml). The filtrate was diluted with 100 ml of water and concentrated. The resulting syrup was dissolved in 700 ml of ethyl acetate and washed with 1 N sodium hydroxide (2×100 ml), water (2×100 ml) and brine (1×100 ml). The organic layer was heated with activated carbon (14 g) and Hyflo SuperCel (14 g) at 60° C. for 1 h. This mixture was filtered hot and washed with ethyl acetate (100 ml) and then concentrated to a syrup. This syrup was immediately dissolved in 1% ethyl acetate/heptane (700 ml) and stirred for 4 h. The resulting slurry was filtered and dried to give the titled compound as a white crystalline solid (3, 68 g, 89% yield, >99% ee)

Alternative crystallization method: The crude product syrup/solid (10 g) was dissolved in MTBE (10 ml) and diluted with heptane (200 ml). The solution was concentrated to about 70 ml under reduced pressure. This mixture was stirred at rt overnight and the resulting slurry was filtered and dried to give the title compound (3, 8.8 g) as a white crystalline solid. m.p.: 107.6° C. [α]=−31.85 (c 1.067, ethanol). LC-MS (ESI): MH+=283.1.

$^1$H NMR (CDCl$_3$): δ 7.66 (m, 2H), 7.56 (d, J=8.2 Hz, 2H), 7.42 (t, J=7.8 Hz, 2H), 7.20 (m, 1H), 7.14 (m, 1H), 6.95 (m, 1H), 5.82 (q, J=6.6 Hz, 1H), 3.85 (s, 3H), 2.63 (br s, 1H). $^{13}$C NMR (CDCl$_3$): δ 160.3, 142.6, 142.2, 133.5, 130.3, 128.3, 127.8, 124.8 (q, J=282 Hz), 120.1, 113.4, 113.3, 73.0 (q, J=32 Hz), 55.7. $^{19}$F NMR (CDCl$_3$): δ −78.3 (d, J=6.4 Hz).

Residual palladium: 11 ppm. Anal. Calcd for $C_{15}H_{13}F_3O_2$: C, 63.83; H, 4.64. Found: C, 63.78; H, 4.60.

5.6. (R)-2,2,2-Trifluoro-1-(3'-methoxybiphenyl-4-yl)ethanol (3)

A 22-L, round-bottom flask equipped with a mechanical stirrer, a thermocouple attached to a temperature controller, and a condenser with a nitrogen line was charged with compound 2 (1.00 kg, 1 wt, 3.92 mol) and ethanol (4.5 L, 4.5 vol). The mixture was sparged with nitrogen for 10 min and (Ph$_3$P)$_2$PdCl$_2$ (12.6 g, 0.0126 wt, Strem) was added. Following additional sparging with nitrogen, a solution of K$_2$CO$_3$ (1.63 kg, 3 equiv) in water (2 vol) was added. The mixture was heated to 75° C. under nitrogen and then approximately 20% of a solution of 3-methoxy phenylboronic acid (715 g, 4.70 mol, 1.2 equiv, Usun) in ethanol (4.5 vol) was added via a peristaltic pump. After 20 min, an in-process control (IPC) sample was taken and showed that the boronic acid had been consumed. This process was repeated until all of the boronic acid was added. After stirring for a further 20 min, HPLC analysis showed that the reaction was complete. The heat was switched off and at 69° C., water (3.6 vol) was added. The reaction mixture was then filtered at 50° C. through a pad of celite (Celpure P300, 0.15 wt., Sigma) and the filter cake was washed with methanol (2×2.5 vol). The filtrate was concentrated under reduced pressure at 40-45° C. to 5 vol. The slurry was then transferred to a separatory funnel and MTBE (10 vol) was added. The mixture was then washed with a 50% solution of sodium hydroxide (0.6 vol). After stirring, the layers were separated and the aqueous phase was extracted with MTBE (1.5 vol). The organic extracts were combined and washed with water (1 vol) followed by 20% aqueous sodium chloride (1 vol) to provide 11.9 volumes of organic product solution. The solution was transferred to a reactor, treated with a slurry of Darco G-60 (0.3 wt) in MTBE (1 vol) and heated to 50° C. After 90 min, the mixture was filtered through a pad of Celpure P300 (0.15 wt) and washed with MTBE (2×3 vol).

The filtrate (14.8 vol) was transferred to a reactor and distilled under vacuum at 45° C. to remove MTBE. The filtrate was reduced to 6.7 volumes over 2.5 hours and then heptane (3.15 vol) was added. The solution was further distilled at 50° C. to 6.7 vol over 1 h and then additional heptane (3.15 vol) was added. The solution was concentrated to 6.7 vol at 55° C. over 1.5 h and then heptane was added (3.15 vol). Precipitation was observed immediately and the distillation was continued under vacuum at 60° C. After 2.5 h, the distillation was stopped (7 vol remaining), the heat was switched off and the batch was cooled overnight to ambient temperature. The batch was filtered at 24° C. and washed with heptane (1.5 vol). The solids were dried at room temperature under vacuum over the weekend to provide 799.7 g of 3 as a white solid [72% yield, >99% (AUC)].

5.7. (R)-2,2,2-Trifluoro-1-(3'-fluorobiphenyl-4-yl)ethanol

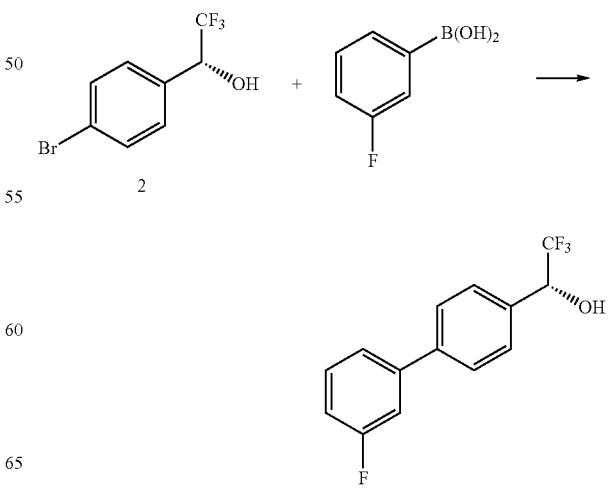

Similar to the above procedure, the title compound was prepared from (R)-1-(4-bromophenyl)-2,2,2-trifluoroethanol (2) and 3-fluorophenylboronic acid. $^1$H NMR (CDCl$_3$): δ 7.62(d, J=6.0 Hz, 2H), 7.56 (d, J=6.3 Hz, 2H), 7.42 (m, 2H), 7.28 (m, 1H), 7.06 (m, 1H), 5.82 (q, J=5.1 Hz, 1H).

5.8. (S)-Methyl 2-(tert-butoxycarbonylamino)-3-(4-(trifluoromethylsulfonyloxy)phenyl)propanoate (5)

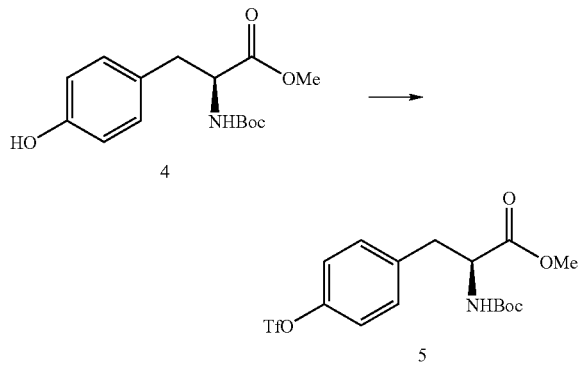

This compound was prepared based on a literature procedure (Shieh, et al. *J. Org. Chem.,* 1992, 57, 379-381). To a solution of Boc-Tyr-OMe (4, Bachem, California, 100 g, 0.34 mol) and N-methylmorpholine (51 g, 1.5 eq) in dichloromethane (1000 ml) was added triflic anhydride (100 g, 1.05 eq) over 2 h at −5 to −15° C. The resulting red solution was stirred at −10° C. for 10 min. HPLC analysis showed complete disappearance of starting material. The reaction was quenched with 10% citric acid (500 ml). The organic layer was washed with 10% citric acid (500 ml) followed by water (500 ml). The resulting light pink solution was concentrated under reduced pressure to 200 ml. This was diluted with acetonitrile (600 ml) and further concentrated to a 200 g solution. This solution was used in the next step without further purification. Estimated yield is 98% by stripping a sample to dryness to give a low melting pale yellow solid. LC-MS (ESI): MH$^+$=428.0, MNH$_4$$^+$=445.0. $^1$H NMR (CDCl$_3$) δ 7.16 (m, 4H), 4.95 (d, J=7.1 Hz, 1H), 4.53 (m, 1H), 3.64 (s, 3H), 3.10 (dd, J$_1$=5.7 Hz, J$_2$=13.8 Hz, 1H), 2.97 (dd, J$_1$=6.3 Hz, J$_2$=13.6 Hz, 1H), 1.34 (s, 9H). $^{13}$C NMR (CDCl$_3$) δ 172.3, 155.4, 149.0, 137.4, 131.5, 121.7, 119.1 (q, J=321 Hz), 80.54, 54.62, 52.7, 38.3, 28.6. $^{19}$F NMR (CDCl$_3$) δ −73.4.

5.9. (S)-2-(Tert-butoxycarbonylamino)-3-(4-(4,4,5,5-tetramethyl-1,3,2-dioxaborolan-2-yl)phenyl)propanoic acid (7)

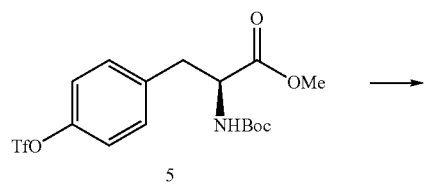

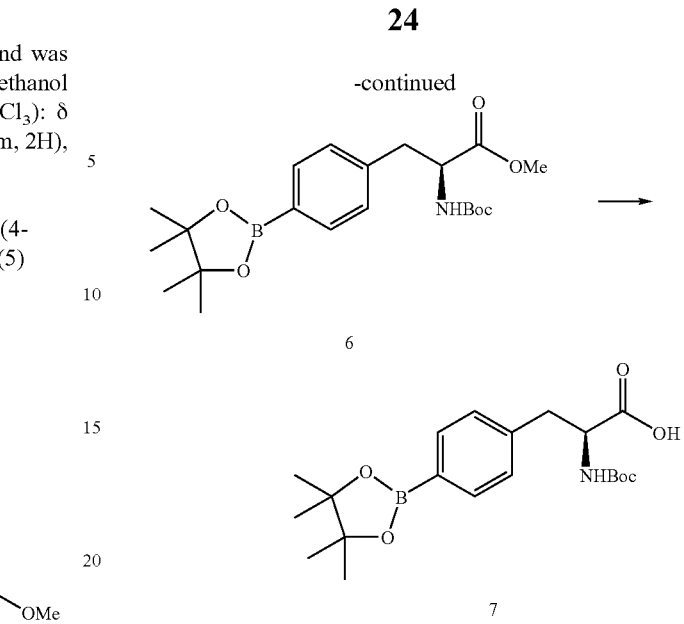

This ester compound 6 was prepared based on a literature procedure (Firooznia, et al., *Tetrahedron Lett.,* 1999, 40, 213-216). Bis(pinacolato)diboron (90 g, 1.1 eq), potassium acetate (63 g, 2 eq), tricyclohexylphosphine (2.3 g, 2.5% mol), and palladium acetate (0.72 g, 1 mol %) were mixed in acetonitrile (950 ml) and the resulting mixture stirred at r.t. for 5 min. The above triflate (5) solution (190 g, 0.32 mol) was added and the resulting mixture was heated at 80° C. for 1 h and cooled. HPLC showed complete consumption of the starting material. The reaction mixture was quenched with aqueous potassium bicarbonate solution (57 g in 475 ml water) and resulting mixture was stirred at r.t. for 30 min. The mixture was filtered through a pad of 20μ cellulose to remove palladium black. A sample of the organic layer was concentrated and purified by column chromatography (gradient: 1:10 to 1:4 ethyl acetate/hexanes) to give the ester compound 6 as a clear oil. LC-MS (ESI): MH$^+$=406.2, MNH$_4$$^+$=423.2, M$_2$H$^+$=811.5, M$_2$NH$_4$$^+$=428.5. $^1$H NMR (CDCl$_3$) δ 7.76 (d, J=8.1 Hz, 2H), 7.15 (d, J=7.6 Hz, 2H), 4.96 (d, J=7.3 Hz, 1H), 4.60 (m, 1H), 3.72 (s, 3H), 3.13 (m, 2H), 1.44 (s, 9H), 1.36 (s, 12H).

The above organic layer of 6 was stirred with aqueous lithium hydroxide solution (23 g in 500 ml water) at r.t. for 30 min. The pH of the resulting slurry was adjusted to about 10 with 6 N hydrochloric acid and filtered. The cake was washed with water (200 ml). Acetonitrile was removed from the filtrate under reduced pressure to give an aqueous slurry (950 ml, additional water was added during distillation). The slurry was filtered through a pad of 20μ cellulose and washed with water (200 ml). The filtrate was washed with MTBE (500 ml) and rediluted with 700 ml MTBE. The mixture was acidified to pH about 4.5 with 6 N hydrochloric acid. The organic layer was washed with water (500 ml) and concentrated under reduced pressure to the titled product (7) as a brown oil (206 g, 95% yield based on estimated purity by NMR). The crude product was used directly in the following step. LC-MS (ESI): MH$^+$=392.2, MNH$_4$$^+$=409.2, M$_2$H$^+$=783.4, M$_2$NH$_4$$^+$=800.4. $^1$H NMR (CDCl$_3$) δ 7.95 (br s, 1H), 7.76 (d, J=7.8 Hz, 2H), 7.21 (d, J=7.6 Hz, 2H), 5.03 (d, J=7.8 Hz, 1H), 4.62 (m, 1H), 3.18 (m, 2H), 1.43 (s, 9H), 1.35 (s, 12H). $^{13}$C NMR (CDCl$_3$) δ 175.8, 155.7, 139.7, 135.4, 129.2, 84.2, 80.5, 54.5, 38.3, 28.7, 25.2.

Compound 7 can optionally isolated by crystallization. Thus, the above MTBE solution of 7 can be dried with anhydrous $Na_2SO_4$ and concentrated to about 1.0 vol under vacuum. Heptane (2.5 vol) was added and concentrated to about 1.5 vol under vacuum. Heptane (4.2 vol) was added slowly at 36~42° C. followed by cooling slowly to 5~10° C. The resulting slurry is filtered, washed by heptane, and dried under vacuum at 20-30° C. to give the product 7 in about 76% yield.

5.10. Alternative Crystallization of (S)-2-(Tert-butoxycarbonylamino)-3-(4-(4,4,5,5-tetramethyl-1,3,2-dioxaborolan-2-yl)phenyl)propanoic acid (7)

A 1 L jacketed three-necked round bottom flask with mechanical stirrer, rubber septum with temperature probe, and gas bubbler was charged with 100 ml of an ethanol solution containing 50.88 g 7. The solution was set stirring under nitrogen, diluted with 35 ml ethanol, then with 50 ml 2-propanol, and was heated to ~60° C. Then 250 ml water were added to reach the cloudy point and the turbid solution was held at ~60° C. for 75 min followed by cooling to ~10° C. over ~1.5 hrs. After 45 min, the mixture was biphasic and was diluted with an additional 30 ml 2-propanol. The mixture was stirred under nitrogen at 10° C. overnight and the resulting white fine suspension was filtered. The collected solids were washed with 100 ml 9:1 water:2-propanol and were dried in vacuo at ~50-60° C. to give 39.88 g 7 as a chalky white powder (78% recovery). The solid was in the filtrate was filtered and dried to afford 4.51 g of a pale yellow granular solid. HPLC suggested this material was mostly the boronic acid 12.

5.11. (S)-3-(4-(2-Amino-6-chloropyrimidin-4-yl)phenyl)-2-(tert-butoxycarbonylamino)propanoic acid (8)

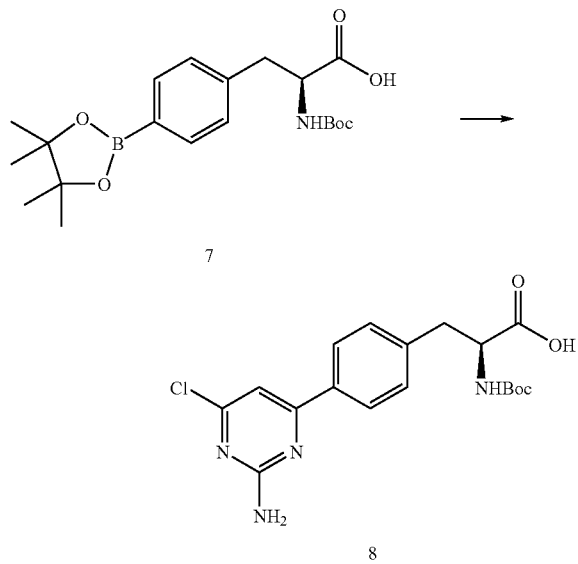

The above crude compound 7 (0.32 mol) was dissolved in ethanol (800 ml) and resulting solution was concentrated under reduced pressure to about 700 ml and diluted with ethanol (1300 ml). To this solution was added 2-amino-4,6-dichloropyrimidine (74 g, 1.4 eq), bis(triphenylphosphine)palladium(II) dichloride (2.3 g, 1 mol %), and aqueous potassium bicarbonate solution (97 g, 3 eq, 380 ml water). This mixture was heated at 75-80° C. for 2 h, at which time HPLC analysis showed complete consumption of the starting material. Ethanol was removed from the filtrate under reduced pressure to give an aqueous slurry (600 ml, additional water was added during distillation). The slurry was filtered and washed with 200 ml water. The cake was dried at 50° C. under vacuum to give recovered 2-amino-4,6-dichloropyrimidine as a tan solid (30 g, 41% of original charge). $^1$H NMR (DMSO-$d_6$) δ 7.58 (br s, 2H), 6.84 (s, 1H). $^{13}$C NMR (DMSO-$d_6$) δ 162.8, 160.9, 107.5. The filtrate was washed with ethyl acetate (400 ml) and diluted with 3:1 THF/MTBE (600 ml). The mixture was acidified to pH about 3.5. The organic layer was washed with brine (300 ml) and concentrated to give the crude product 8 as a red oil (180 g). This oil was redissolved in THF (300 ml), polish-filtered, and washed with THF (100 ml). The filtrate was diluted with isopropanol (400 ml) and the mixture was distilled atmospherically to about 300 ml. More isopropanol (400 ml) was added and distillation continued until the volume reached about 500 ml. The mixture was then cooled over 1 h to 45° C. and held for 2 h before it was cooled to r.t. over 1 h. After 1 h hold, the slurry was filtered, washed with isopropanol (150 ml), and dried at 50° C. under vacuum to give the product 8 as a light pink solid (46.2 g, 37% yield from Boc-Tyr-OMe, 4). Purity: 93.4% by HPLC. Chiral purity: >99% ee. Chiral analysis was performed on the corresponding methyl ester derivative, which was prepared using trimethylsilyldiazomethane. An analytical pure sample was obtained by column chromatography (gradient 1:20 to 1:10 methanol/dichloromethane). LC-MS (ESI) MH$^+$=393.1, MH$^+$+acetonitrile=434.1, M$_2$H$^+$=785.3. $^1$H NMR (DMSO-$d_6$) δ 12.60 (s, 1H), 8.02 (d, J=8.3 Hz, 2H), 7.38 (d, J=8.1 Hz, 2H), 7.23 (s, 1H), 7.13 (br s, 2H), 3.09 (dd, $J_1$=4.4 Hz, $J_2$=13.5 Hz, 1H), 2.91 (dd, $J_1$=10.5 Hz, $J_2$=13.8 Hz, 1H), 1.32 (s, 9H). $^{13}$C NMR (DMSO-$d_6$) δ 173.4, 165.8, 163.5, 161.0, 155.4, 141.4, 134.0, 129.4, 126.8, 104.4, 78.0, 54.8, 36.2, 28.1. Anal. Calcd for $C_{18}H_{21}ClN_4O_4$: C, 55.03; H, 5.39; N, 14.26. Found: C, 54.76; H, 5.65; N, 14.09.

HPLC analysis of the above mother liquor against an standard solution of compound 8 showed additional 38 g product 8 (30% yield from Boc-Tyr-OMe, 4). Product 8 can be partially recovered by further concentration of the mother liquor to give a total yield of 60% from Boc-Tyr-OMe, 4.

5.12. (S)-3-(4-(2-Amino-6-chloropyrimidin-4-yl)phenyl)-2-(tert-butoxycarbonylamino)propanoic acid (8)

A 22-L, round-bottom flask equipped with a mechanical stirrer, a thermocouple attached to a temperature controller, and a condenser with a nitrogen line was charged with compound 7 (850 g, 1 wt, 2.17 mol), 2-amino-4,6-dichloropyrimidine (712.3 g, 2 equiv, Usun), and ethanol (13.6 L, 16 vol). The slurry was sparged with nitrogen for 10 min; then (Ph$_3$)$_2$PdCl$_2$ (18.3 g, 0.021 wt, Strem) was added and nitrogen sparging was continued for 10 min. A solution of potassium bicarbonate (783 g, 3.6 equiv) in water (3.2 L, 3.7 vol) was then charged to the reactor whereupon gas evolution was observed. The mixture was heated to 75° C. for a total of 11.5 h and then cooled to 45° C. overnight. HPLC analysis after 9.5 h at 75° C. indicated that there were about 3.0% of 7 remaining (by conversion). The reaction was cooled to 45° C. and stirred overnight whereupon HPLC analysis indicated that there was <1.0% of 7 remaining.

The batch was then distilled under reduced pressure at 45° C. over a period of 15 h to afford 4-5 L of a yellow slurry. The batch was then allowed to cool overnight. Water was added (3 vol) and after heating to 45° C., distillation was continued for 1 h until no more distillate was collected. The vacuum was released and water (3 vol) was added to the batch. After allowing to settle, the batch was filtered through a slurry of cellulose powder (20 micron, 0.2 wt.) in water (1 vol). Water (2 vol) was added to the remaining solids/slurry in the reactor and this was filtered through a sintered glass funnel. This filtrate was then further filtered through the cellulose pad to afforded 11.2 L of product solution (13.2 vol).

The solution was then transferred to a separatory funnel containing EtOAc (3.3 vol). After stirring and separating, the aqueous phase was transferred to a 22-L reactor and then a solution of $PBu_3$ (212 ml, 0.25 vol, 97%) in EtOAc (3.5 vol) was charged to the reactor. The solution was heated at 50° C. for 2.5 h. Additional EtOAc (3.3 vol) was added to the reactor and the contents were charged to a separatory funnel and the two phases separated. The aqueous phase (41° C.) was charged back to the separatory funnel and washed with additional EtOAc (3.3 vol). The two phases were separated and then the aqueous phase was charged to a 22-L reactor and heated to 45° C. Heptane (5 vol) was added to the reactor, the contents of the reactor were transferred to a separatory funnel and the two phases were separated. The aqueous phase (11.2 L, 13.2 vol) was charged to the 22-L reactor, diluted to 14 vol with water and then a slurry of Darco G-60 (0.2 wt) in water (1 vol) was charged to the reactor. The mixture was heated to 60° C. and stirred at 60° C. for 2 h. The heat was switched off and the batch was stirred over the weekend. The batch was filtered through a pad of Celpure P300 (0.2 wt, Sigma) and washed with water (2×1.2 vol).

A 22-L, round-bottom flask equipped with a mechanical stirrer, a thermocouple attached to a temperature controller, and pH probe attached to a pH meter was charged with citric acid (127.5 g, 0.15 wt) and water (2 vol). The solution was heated to 40° C. and the pH of the solution was adjusted to 4.0 with a 2 M solution of sodium hydroxide. A solution of citric acid (40 wt %, 2 L) was charged to an addition funnel and was attached to the reactor. The basic solution of 8 was then transferred via peristaltic pump through an in-line filter to the citric acid solution and the pH was maintained at pH 4.0 with the 40% citric acid solution. Once the addition was complete, the batch was heated to 60° C. and stirred for 2 h. The batch was then cooled overnight and the solids were filtered at 29° C. The cake was washed with water (2×2.5 vol) and then dried at 45-50° C. for 24 h to provide 720 g of 8 (84% yield) with a purity of 85.9% (AUC).

5.13. Optional Purification of (S)-3-(4-(2-Amino-6-chloropyrimidin-4-yl)phenyl)-2-(tert-butoxycarbonylamino)propanoic acid (8)

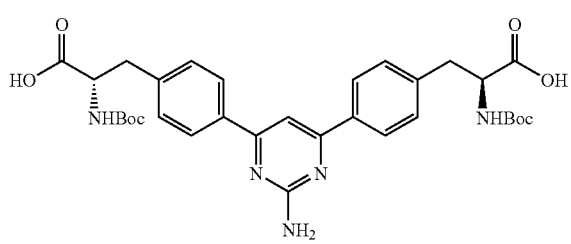

A

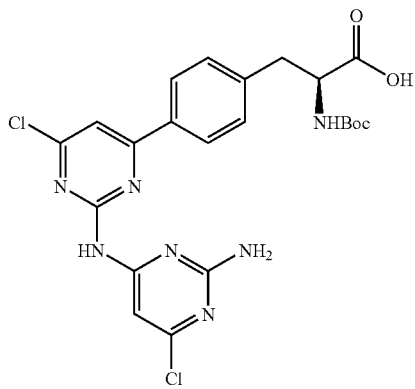

B

The crude 8 as prepared from examples 5.11 or 5.12 is impure and usually contains about 6% of the diacid impurity (A) and about 4% amination product (B). This material can be used directly in the next step or it can optional purified by the following methods.

Method 1. To a 3-necked 250 ml RB flask was added crude 8 (10.0 g, 25.4 mmol, 90% pure, with 6% A and 4% B), i-PrOH/toluene (1:1, 80 ml/80 ml, 8×/8×) and tert-butylamine (13.4 ml, 5.0 equiv). The resulting mixture was stirred and heated at 78° C. for 1 hour and then slowly cooled to 0° C., and stirred for another hour. The solids were collected by filtration and the cake was washed with 20 ml of i-PrOH/toluene (1:3). The cake was dried under vacuum to constant weight to provide the desired tert-butylamine salt of 8 as a pale yellow solid (8.8 g, 74% yield, 94% pure, 3% A, 3% B).

To a 3-necked 250 ml RB flask was added the tert-butylamine salt of 8 (20.0 g, 42.9 mmol) and followed by $H_2O$/THF/toluene (400 ml/200 ml/160 ml, 20×/10×/8×). The resulting mixture was heated to 60° C. and slowly added 6M HCl until pH of the mixture reached 4.0. The mixture was cooled to room temperature and the organic layer was separated. The organic layer was washed with $H_2O$ (100 ml, 5×) and concentrated by rotary evaporating to around 160 ml of overall volume. The solids were collected by filtration and the cake was washed with 20 ml of toluene. The cake was dried under vacuum to constant weight to provide 8 as a pale yellow solid (15.0 g, 89% yield, 94% pure, 3% A, 3% B).

Method 2. To a 3-necked 250 ml RB flask was added crude 8 (20.0 g, 42.9 mmol, 90% pure, with 6% A and 4% B) and followed by THF/toluene (200 ml/160 ml, 10×/8×). The resulting mixture was heated to 60° C. for 1 h and cooled to room temperature. THF was removed by rotary evaporating to around 160 ml of overall volume. The solids were collected by filtration and the cake was washed with 20 ml of toluene. The cake was dried under vacuum to constant weight to provide 8 as a pale yellow solid (11.8 g, 70% yield, 92.8% pure, 6.0% A, 1.3% B).

To a 3-necked 250 ml RB flask was added the above 8 (10.0 g, 25.4 mmol) and tert-butylamine (13.4 ml, 5 equiv) followed by i-PrOH/toluene (1:1, 80 ml/80 ml, 8×/8×). The resulting mixture was heated to clear (78° C.) for 1 hour, slowly cooled to 0° C., and stirred at 0° C. for another 1 hour. The solids were collected by filtration and the cake was washed with 20 ml of i-PrOH/toluene (1:3). The cake was dried under vacuum to constant weight to provide the tert-butylamine salt of 8 as a pale yellow solid (9.7 g, 82% yield, 96% pure, 3.3% A, 0.6% B).

To a 3-necked 250 ml RB flask was added the tert-butylamine salt of 8 (20.0 g, 42.9 mmol) and followed by $H_2O$/THF/toluene (400 ml/200 ml/160 ml, 20×/10×/8×). The resulting mixture was heated to 60° C. and slowly added 6M HCl until pH of the mixture reached 4.0. The mixture was cooled to room temperature and the aqueous layer was separated. The organic layer was washed with H₂O (100 ml, 5×) and concentrated by rotary evaporating to around 160 ml of overall volume. The solids were collected by filtration and the cake was washed with 20 ml of toluene. The cake was dried under vacuum to constant weight to provide 8 as a pale yellow solid (15 g, 88% yield, 96% pure, 3.3% A, 0.5% B).

Method 3. To a 3-necked 3 L RB flask was added the aqueous solution of the potassium salt containing ~50 g 8 (90%, 6% A, 4% B, all normalized AUC) and followed by THF/toluene (500 ml/400 ml, 10×/8×). The resulting mixture was heated to 60° C. and slowly added 6M HCl until pH of the mixture reached 4.0. The mixture was cooled to room temperature and the aqueous layer was separated. The organic layer was washed with H₂O (250 ml, 5×) and concentrated by rotary evaporating to around 400 ml of overall volume to afford a slurry of 8 in ~8× toluene.

To a 3-necked 3 L RB flask was added the slurry (in 8× toluene, 400 ml) and tert-butylamine (67 ml, 5.0 equiv) followed by i-PrOH (400 ml, 8×). The resulting mixture was heated at 78° C. for 1 hour, cooled to 0° C., and stirred at 0° C. for another 1 hour. The solids were collected by filtration and the cake was washed with 100 ml of i-PrOH/toluene (1:3). The cake was dried under vacuum to constant weight to provide the tert-butylamine salt of 8 as a pale yellow solid (42.4 g, 72% yield, 95% pure, 3.2% A, 1.9% B).

To a 3-necked 250 ml RB flask was added the tert-butylamine salt of 8 (42.4 g, 91.0 mmol) and followed by H₂O/THF/toluene (1000 ml/500 ml/400 ml, 20×/10×/8×). The resulting mixture was heated to 60° C. and slowly added 6M HCl until pH reached 4.0. The mixture was cooled to room temperature. The organic layer was separated and washed with H₂O (250 ml, 5×). The organic solution was concentrated by rotary evaporating to ~400 ml of overall volume. The solids were collected by filtration and the cake was washed with 100 ml of toluene. The cake was dried under vacuum to constant weight to provide 8 as a pale yellow solid (35.4 g, 89.5% yield, 96% pure, 2.9% A, 1.6% B).

Method 4. To a test tube was added 8 (198.6 mg, 0.5 mmol) and cinchonidine (167.1 mg) followed by acetonitrile (7.5 ml). The resulting mixture was heated to clear and cooled to room temperature, and stirred for another 2 hours. The solids were collected by filtration and the cake was washed with 1 ml of MTBE. The cake was dried under vacuum to constant weight to provide the final product (208 mg, 68% yield, 92% pure, 4.4% A, 1.4% B).

5.14. Preparation of (S)-3-(4-(2-Amino-6-chloropyrimidin-4-yl)phenyl)-2-(tert-butoxycarbonylamino) propanoic acid (8) using potassium carbonate as base To a 500 ml 3-neck round-bottom flask equipped with a mechanical stirrer, a thermocontroller was charged 2-amino-4,6-dichloropyrimidine (12.57 g, 1.5 equiv), boronate compound 7 (20.00 g, 51.1 mmol), potassium carbonate (21.19 g, 3.0 equiv) and ethanol/water (200 ml, 5:1 by volume). The mixture was stirred and the catalyst bis(triphenylphosphine)palladium(II) dichloride (359 mg, 1 mol %) was added. The mixture was heated to 80° C. and stirred for 2 h. The reaction was cooled to room temperature and diluted with water (100 ml). The mixture was then concentrated under reduced pressure to remove most of ethanol and 1 N NaOH (60 ml) was added. The mixture was extracted twice with ethyl acetate (2×200 ml) and the aqueous layer was acidified to pH ~3 using 1 N HCl. The mixture was extracted with ethyl acetate twice (200 ml and 100 ml, respectively) and the combined organic layers were concentrated and the residue was purified by column chromatography (gradient 1:20 to 1:10 methanol/dichloromethane) to afford compound 8 as a pale yellow solid (15.92 g, 79%).

5.15. Preparation of (S)-3-(4-(2-Amino-6-chloropyrimidin-4-yl)phenyl)-2-(tert-butoxycarbonylamino) propanoic acid (8) using the lithium salt of (S)-2-(tert-butoxycarbonylamino)-3-(4-(4,4,5,5-tetramethyl-1,3,2-dioxaborolan-2-yl)phenyl) propanoic acid (7)

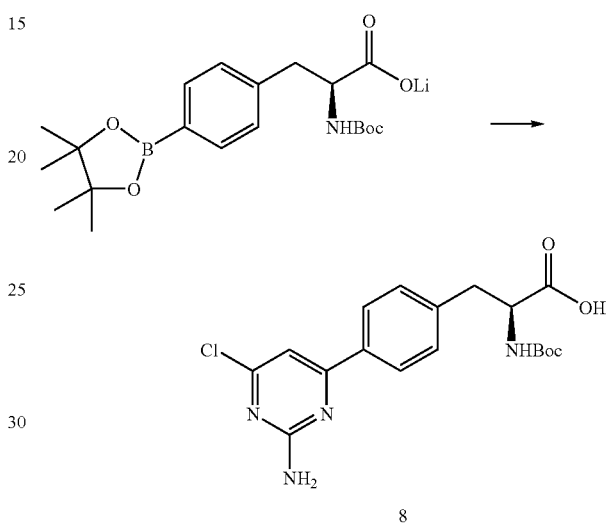

During preparation of compound 7, the isolation of the free acid can be optionally omitted. Thus, an aqueous solution of the lithium salt of compound 7 in 100 ml water, prepared from 5.0 g of Boc-Tyr-OMe (4, 17 mmol), was mixed 2-amino-4,6-dichloropyrimidine (3.3 g, 1.2 eq), potassium bicarbonate (5.0 g, 3 eq), bis(triphenylphosphine)palladium(II) dichloride (60 mg, 0.5 mol %), and 100 ml ethanol. The resulting mixture was heated at 70° C. for 5 h. Additional 2-amino-4,6-dichloropyrimidine (1.1 g, 0.4 eq) was added and heating was continued at 70° C. for 2 h more. HPLC analysis showed about 94% conversion. Upon cooling and filtration, the filtrate was analyzed by HPLC against a standard solution of compound 8. The assay indicated 3.9 g compound 8 was contained in the solution (59% yield from compound 4).

5.16. Alternative Procedure for Preparation of (S)-3-(4-(2-Amino-6-chloropyrimidin-4-yl)phenyl)-2-(tert-butoxycarbonylamino)propanoic acid (8) using potassium carbonate as base

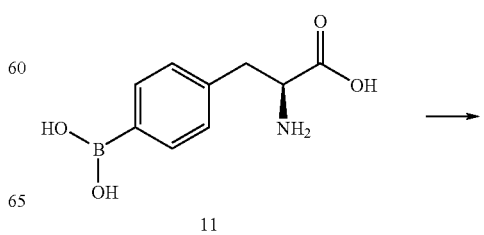

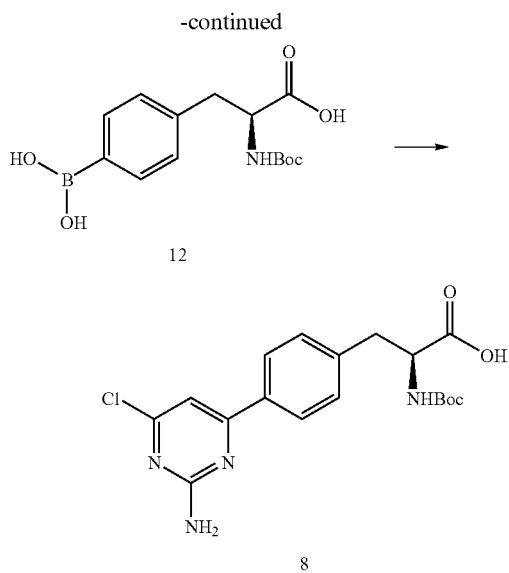

The boronic acid compound 11 (Ryscor Science, Inc., North Carolina, 1.0 g, 4.8 mmol) and potassium carbonate (1.32 g, 2 eq) were mixed in aqueous ethanol (15 ml ethanol and 8 ml water). Di-tert-butyldicarbonate (1.25 g, 1.2 eq) was added in one portion. After 30 min agitation at r.t., HPLC analysis showed complete consumption of the starting compound 11. The 2-amino-4,6-dichloropyrimidine (1.18 g, 1.5 eq) and the catalyst bis(triphenylphosphine)palladium(II) dichloride (34 mg, 1 mol %) were added and the resulting mixture was heated at 65-70° C. for 3 h. HPLC analysis showed complete consumption of compound 12. After concentration and filtration, HPLC analysis of the resulting aqueous solution against a standard solution of compound 8 showed 1.26 g compound 8 (67% yield).

5.17. Alternative procedure for preparation of (S)-3-(4-(2-Amino-6-chloropyrimidin-4-yl)phenyl)-2-(tert-butoxycarbonylamino)propanoic acid (8) using potassium carbonate/potassium bicarbonate as base

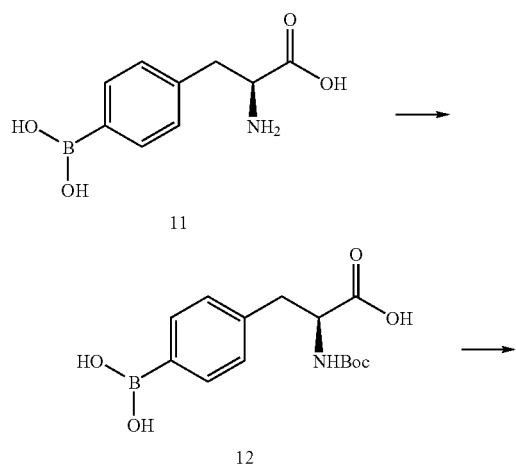

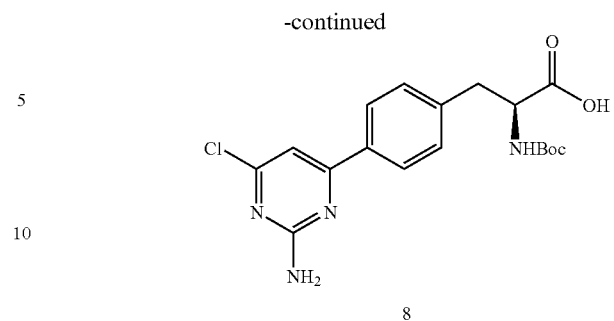

The boronic acid compound 11 (10 g, 48 mmol) and potassium bicarbonate (14.4 g, 3 eq) were mixed in aqueous ethanol (250 ml ethanol and 50 ml water). Di-tert-butyldicarbonate (12.5 g, 1.2 eq) was added in one portion. HPLC analysis indicated that the reaction was not complete after overnight stirring at r.t. Potassium carbonate (6.6 g, 1.0 eq) and additional di-tert-butyldicarbonate (3.1 g, 0.3 eq) were added. After 2.5 h agitation at r.t., HPLC analysis showed complete consumption of the starting compound 11. The 2-amino-4,6-dichloropyrimidine (11.8 g, 1.5 eq) and the catalyst bis(triphenylphosphine)-palladium(II) dichloride (0.34 g, 1 mol %) were added and the resulting mixture was heated at 75-80° C. for 2 h. HPLC analysis showed complete consumption of compound 12. The mixture was concentrated under reduced pressure and filtered. The filtrate was washed with ethyl acetate (200 ml) and diluted with 3:1 THF/MTBE (120 ml). This mixture was acidified to pH about 2.4 by 6 N hydrochloric acid. The organic layer was washed with brine and concentrated under reduced pressure. The residue was precipitated in isopropanol, filtered, and dried at 50° C. under vacuum to give compound 8 as an off-white solid (9.0 g, 48% yield). Purity: 92.9% by HPLC analysis. Concentration of the mother liquor yielded and additional 2.2 g off-white powder (12% yield). Purity: 93.6% by HPLC analysis.

5.18. (S)-3-(4-(2-Amino-6-((R)-2,2,2-trifluoro-1-(3'-methoxybiphenyl-4-yl)ethoxy)pyrimidin-4-yl)phenyl)-2-(tert-butoxycarbonylamino)propanoic acid

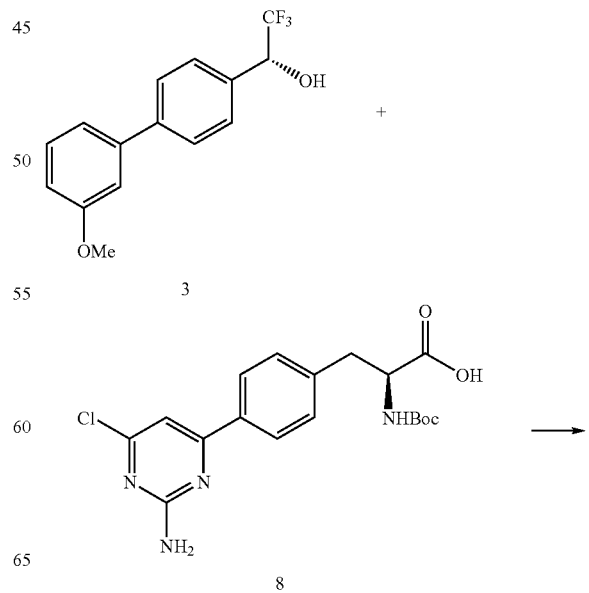

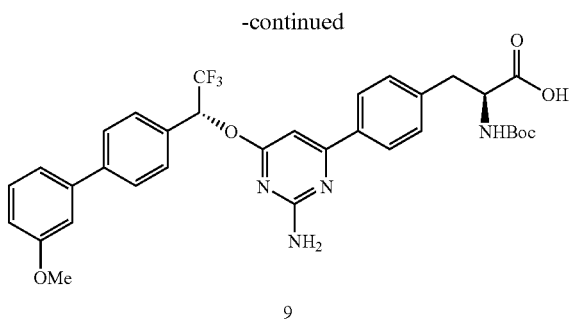

9

To a 250 ml 3-neck round-bottom flask equipped with a mechanical stirrer, a thermocontroller was charged monochloride 8 (20.39 g, 51.9 mmol), alcohol 3 (17.58 g, 1.2 equiv), cesium carbonate (84.55, 5.0 equiv) and dioxane (205 ml). The mixture was heated to 100° C. and stirred for 17 h. The reaction was cooled to room temperature and diluted with water (80 ml). Two phases were split and the organic layer was collected and diluted with ethyl acetate (200 ml), washed with a mixture of brine (50 ml) and 1 N HCl (50 ml). The organic layer was concentrated and the residue was purified by column chromatography (gradient: 1:30 to 1:20 methanol/dichloromethane and 0.5% acetic acid) to afford compound 9 as a yellow solid. This solid was recrystallized from EtOH and heptane to give 21.78 g pale yellow solid. Further crystallization of the mother liquor gave 2.00 g pale yellow solid (overall 23.78 g, 72% yield). Chiral analysis of the corresponding methyl ester derivative, prepared using trimethylsilyldiazomethane, showed no detectable amount of the diastereomers. LC-MS (ESI): MH$^+$=639.2. $^1$H NMR (DMSO-d$_6$) δ 12.60 (br s, 1H), 8.00 (d, J=8.0 Hz, 2H), 7.77 (d, J=8.0 Hz, 2H), 7.67 (d, J=8.0 Hz, 2H), 7.37 (m, 3H), 7.21 (m, 2H), 7.13 (d, J=8.0 Hz, 1H), 6.96 (m, 1H), 6.84 (m, 2H), 6.75 (s, 2H, 4.15 (m, 1H), 3.82 (s, 3H), 3.10 (dd, J=13.6, 4.4 Hz, 1H), 2.89 (dd, J=13.6, 10.4 Hz, 1H), 1.32 (s, 9H). $^{13}$C NMR (DMSO-d$_6$) δ 173.4, 168.4, 166.1, 162.9, 159.7, 155.4, 141.5, 140.8, 134.8, 130.7, 130.0, 129.3, 128.4, 127.2, 126.6, 124.1 (q, J=281 Hz), 119.1, 113.4, 112.3, 91.3, 78.0, 71.3 (q, J=30 Hz), 55.1, 54.9, 36.2, 28.1. $^{19}$F NMR (DMSO-d$_6$): δ −74.6 (d, J=7.2 Hz). Anal. Calcd. for C$_{33}$H$_{33}$F$_3$N$_4$O$_6$: C, 62.06; H, 5.21; N, 8.77. Found: C, 62.25; H, 5.10; N, 8.69.

5.19. Preparation of (S)-3-(4-(2-Amino-6-((R)-2,2,2-trifluoro-1-(3'-methoxybiphenyl-4-yl)ethoxy)pyrimidin-4-yl)phenyl)-2-(tert-butoxycarbonylamino)propanoic acid under various conditions Using similar procedure, various reaction conditions were examined. The results are listed in the table below.

| entry | equiv of 3 | base (x, equiv) | additive | time (h) | % conversion (isolated yield)[a] |
|---|---|---|---|---|---|
| 1 | 1.2 | Cs$_2$CO$_3$ (5.0) | — | 17 | 97 (72) |
| 2 | 1.2 | NaH (5.0) | — | 1 | —[b] |
| 3 | 1.2 | NaOt-Bu (3.0) | — | 1 | —[c] |
| 4 | 1.2 | NaOt-Am (3.0) | — | 1 | —[c] |
| 5 | 1.2 | DBU (5.0) | — | 24 | 0 |
| 6 | 1.2 | tetramethylguanidine (5.0) | — | 24 | 0 |
| 7 | 1.2 | K$_2$CO$_3$ (5.0) | — | 24 | 0 |
| 8 | 1.2 | Cs$_2$CO$_3$ (4.0) | — | 20 | 98[d] |
| 9 | 1.2 | Cs$_2$CO$_3$ (4.0) | 10 mol % n-Bu$_4$NHSO$_4$ | 17 | 98[d] |
| 10 | 1.2 | Cs$_2$CO$_3$ (3.0) | 10 mol % n-Bu$_4$NHSO$_4$ | 18 | 98[d] |
| 11 | 1.0 | Cs$_2$CO$_3$ (3.0) | 10 mol % n-Bu$_4$NHSO$_4$ | 18 | 88[d] |

[a]All the reactions were run in 10x dioxane except otherwise noted;
[b]The starting material 1 decomposed;
[c]A complex mixture of starting material, deBoc of starting material, product, deBoc of product was observed.
[d]The reaction was run in 5x dioxane.

5.20. (S)-2-Amino-3-(4-(2-amino-6-((R)-2,2,2-trifluoro-1-(3'-methoxybiphenyl-4-yl)ethoxy)pyrimidin-4-yl)phenyl)propanoic acid (10)

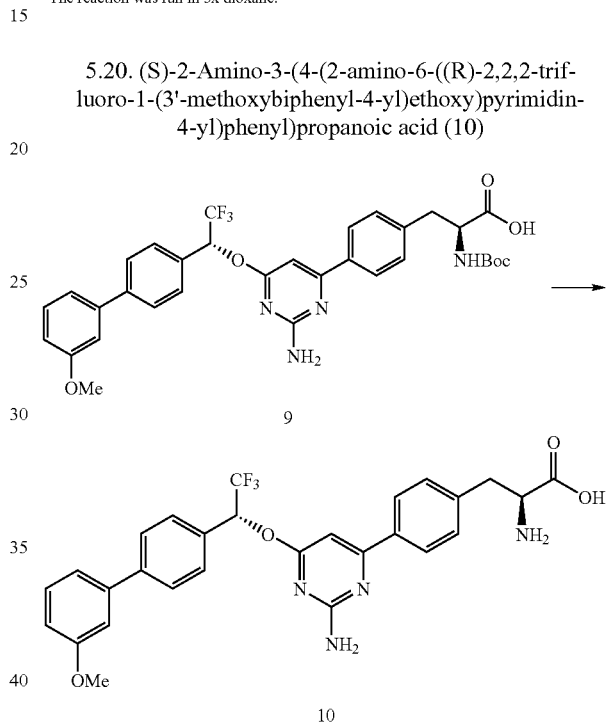

To a 500 ml round-bottom flask was added compound 9 (20.00 g, 31.32 mmol) and THF (100 ml). The solid was dissolved upon stirring and 6 N hydrochloric acid (100 ml) was added slowly. The mixture was then stirred at room temperature for 14 h. The reaction was diluted with water (100 ml) and most of THF was removed under reduce pressure. The resulting aqueous solution was then transferred to a 500 ml three-necked round-bottom flask equipped with a mechanical stirrer, a pH meter, a thermocontroller and an addition funnel. At 60° C., a solution of 50% aqueous sodium hydroxide was added slowly until pH=4, then a solution of 1 N aqueous sodium hydroxide was added until pH reached 6.5. The mixture was stirred at 60° C. for additional 30 min and the solid was collected by filtration and oven-dried under vacuum to give compound 10 (16.30 g, 96% yield) as a pale yellow solid. LC-MS (ESI): MH$^+$=539.1. $^1$H NMR (DMSO-d$_6$) δ 8.01 (d, J=8.0 Hz, 2H), 7.76 (d, J=8.0 Hz, 2H), 7.67 (d, J=8.0 Hz, 2H), 7.38 (m, 3H), 7.23 (m, 2H), 6.96 (d, J=8.0 Hz, 1H), 6.81 (m, 3H), 3.81 (s, 3H), 3.59 (br m, 1H), 3.00 (br m, 1H). $^{13}$C NMR (DMSO-d$_6$) 169.9, 168.4, 166.1, 162.9, 159.7, 141.5, 140.8, 140.8, 140.0, 134.9, 130.7, 130.0, 129.7, 128.4, 127.2, 126.8, 124.1 (q, J=281 Hz), 119.1, 113.4, 112.3, 91.2, 71.4 (q, J=30 Hz), 55.1, 55.0, 36.5.
$^{19}$F NMR (DMSO-d$_6$): δ −74.6 (d, J=6.8 Hz).

5.21. One-Pot Preparation of (S)-2-Amino-3-(4-(2-amino-6-((R)-2,2,2-trifluoro-1-(3'-methoxybiphenyl-4-yl)ethoxy)pyrimidin-4-yl)phenyl)propanoic acid (10)

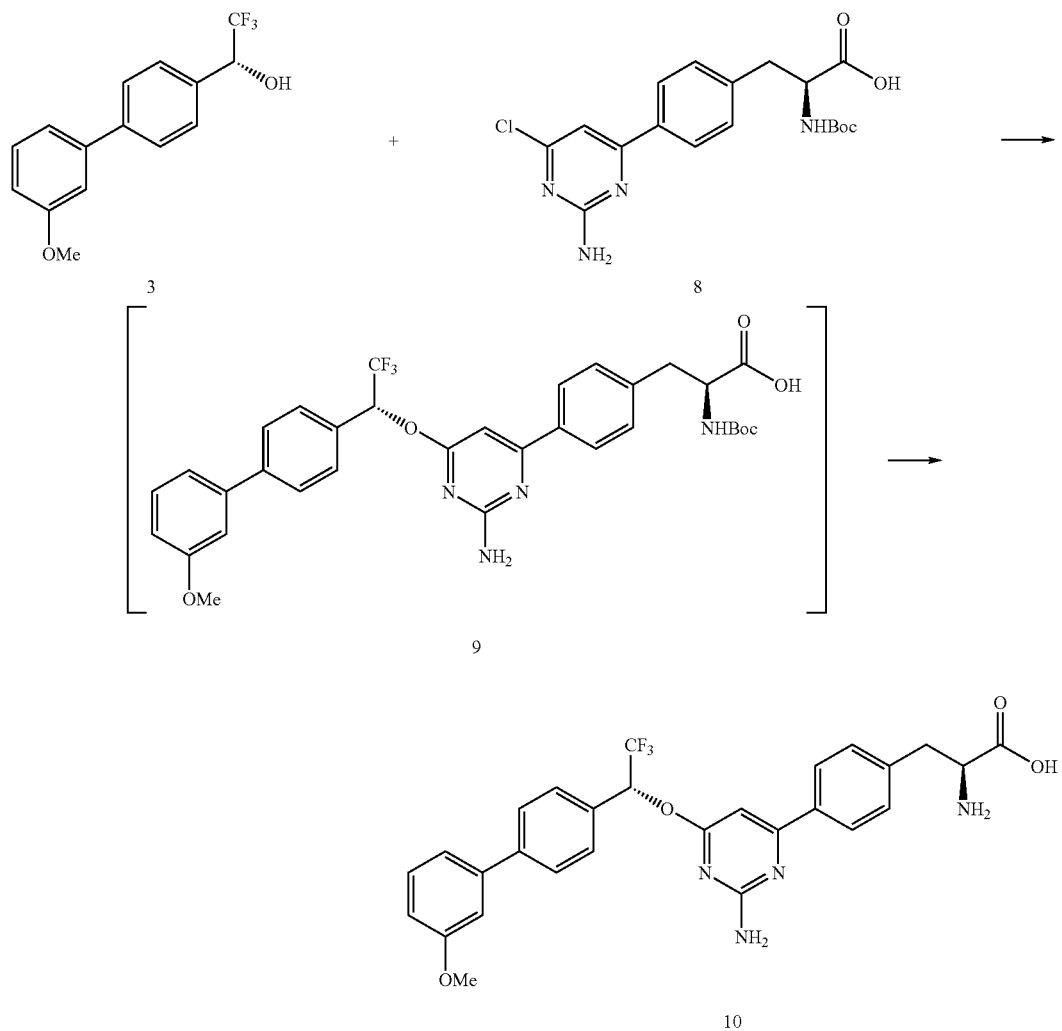

To a 3-neck 250 ml round-bottom flask equipped with a mechanical stirrer, a thermocontroller, was charged compound 3 (8.62 g, 1.2 equiv), 8 (10.00 g, 25.46 mmol), tetrabutylammonium bisulfate (0.86 g, 10 mol %), and cesium carbonate (29.04 g, 3.5 equiv). Dioxane (50 ml) was added and the resulting mixture was heated at 100° C. for 18 h. HPLC analysis showed 99% conversion of the starting material 8. The mixture was cooled down to 60° C. and water (60 ml) was added. The top organic layer was diluted with THF (80 ml), washed with brine (50 ml), transferred to a 500 ml round-bottom flask, and 80 ml of 6 N hydrochloric acid was added. The mixture was stirred at room temperature for 16 h. LC-MS analysis of the reaction mixture showed complete consumption of the intermediate compound 9. The reaction mixture was transferred to a 500 ml separatory funnel. The round-bottom flask was washed with water (2×40 ml) and the washes were also transferred to the funnel. The mixture was washed with ethyl acetate (2×100 ml) and the aqueous layer was collected and concentrated at 40° C. (bath temperature) under 80 mbar vacuum to remove any remaining organic solvents. The resulting aqueous solution was then transferred to a 500 ml three-necked round-bottom flask equipped with a mechanical stirrer, a pH meter, a thermocontroller and an addition funnel. At 60° C., a solution of 50% aqueous sodium hydroxide solution was added slowly until pH=4, then a solution of 1N aqueous sodium hydroxide was added until pH reached 6.5. The mixture was stirred at 60° C. for additional 30 min and the yellow solids were collected by filtration. HPLC analysis of this solid showed a purity of about 95%. The solids were dried under vacuum at 50° C. overnight to give the crude product compound 10 as a yellow solid (9.48 g, 69% overall yield).

The above solids (9.48 g) were transferred to a 500 ml round-bottom flask and water (95 ml) was added. The mixture was heated at 80° C. (bath temperature) and THF (40 ml) was added dissolve the solids. Most of THF was then removed under vacuum at 80° C. The precipitate was added acetonitrile (80 ml) and was stirred at 80° C. for 2 h, cooled down to r.t. and then stirred at 0° C. for 30 min. The solid was collected by filtration, washed with water (2×50 ml) to give compound 10 as a pale yellow solid (8.53 g, 90% recovery, 62% overall yield). HPLC analysis showed a purity greater than 99%.

5.22. One-pot preparation of (S)-2-Amino-3-(4-(2-amino-6-((R)-2,2,2-trifluoro-1-(3'-methoxybiphenyl-4-yl)ethoxy)pyrimidin-4-yl)phenyl)propanoic acid (10)

A 22-L, round-bottom flask equipped with a mechanical stirrer, a thermocouple attached to a temperature controller, and a condenser with a nitrogen line was charged with 1,4-dioxane (4 vol) followed by the addition of $Cs_2CO_3$ (2.03 kg, 3.5 equiv), compound 3 (603 g, 1.2 equiv) and tetrabutylammonium bisulfate (102.8 g, 0.147 wt). The slurry was slowly heated to 70° C. and then a slurry of compound 8 (700.0 g, 1.782 mol, 1 wt) in 1,4-dioxane (1.5 vol) was added in three portions over 10 min. The beaker containing 8 was rinsed with 1,4-dioxane (0.5 vol) and added to the reactor. The reaction became thick briefly after stirring for 15-30 minutes but the entire batch was stirrable. The controller was heated at 78° C. overnight followed by heating at 98° C. for 8 h then 85° C. overnight. HPLC analysis indicated that there were 2.1% of 8 remaining. The reaction was quenched at 78° C. with water (6 vol) and then cooled further. At 42° C., the batch was transferred to a separatory funnel and the two phases separated. The organic phase was then diluted with THF (8 vol) and washed with brine (5 vol). The phases were separated and the organic phase was washed with brine (5 vol). The phases were separated and the organic phase (9.5 L) was transferred to a 22-L reactor. A solution of 6 N HCl (11.4 vol) was added and the batch was heated at 40-45° C. for 2 h. HPLC analysis indicated that the reaction was complete and Darco G-60 (0.33 wt.) and water (2 vol) were added. The batch was stirred at 40° C. over the weekend and then heated to 60° C. The reaction mixture was filtered at 60° C. through PTFE cloth and the reactor was rinsed with water (6 vol). The rinse was heated to 60° C. and washed through the Darco pad. The filtrate was then passed through a 0.3-μm in-line filter and washed with IPAc twice (10 vol, 8.8 vol). The aqueous phase was then concentrated under reduced pressure at 45° C. using a 20-L, rotary evaporator until the mixture turned cloudy (2-3 h). The volume of distillate collected was approximately 3.3 L. The batch was then transferred back to a 22-L reactor and held at 40° C. overnight.

The batch was heated to 60° C. whereupon the batch turned from cloudy to clear. To a separate 22-L reactor was charged water (1.6 vol) and 85% phosphoric acid (0.24 vol) and the pH was adjusted to 6.5 using a 50% NaOH solution (approximately 0.3 vol). The acidic product solution was then transferred via peristaltic pump to the reactor containing the pH 6.5 buffered solution and the pH was maintained within 6 and 7 through the addition of 50% NaOH (approximately 3.5 vol). The temperature of the reactor was maintained between 55 and 65° C. (2-h addition time). Once the addition was complete, the slurry was heated at 60-65° C. for 90 min, filtered, and washed with water (2×6.7 vol). The wet cake was dried in a vacuum oven at 55° C. for 39 h to afford 635 g of crude 10 as a yellow solid (66% yield). The purity of the product was 93.2% (AUC).

5.23. Purification of (S)-2-Amino-3-(4-(2-amino-6-((R)-2,2,2-trifluoro-1-(3'-methoxybiphenyl-4-yl)ethoxy)pyrimidin-4-yl)phenyl)propanoic acid (10)

A 22-L, round-bottom flask equipped with a mechanical stirrer, a thermocouple attached to a temperature controller, and a condenser with a nitrogen line was charged with crude 10 (630 g) followed by the addition of THF (5 vol). The slurry was heated to 65° C. After 30 min, a solution of 5-6 N HCl in IPA (0.47 L, 0.746 vol) was added and the solids slowly dissolved. The orange solution was heated at 65° C. for 30 min IPA (10 vol) was slowly added maintaining the temperature between 60-70° C. Once the addition was complete, the mixture was stirred for 20 min and then IPAc (10 vol) was slowly added maintaining the temperature between 60-70° C. Once the addition was complete, the thick slurry was stirred at 65° C. for 1 h and then cooled to 27° C. over 4.5 h. The solids were filtered and washed with IPA (2×3 vol). The product was dried in a vacuum oven at 55° C. for 15 h to afford 630 g of 10 diHCl salt (88% yield) with a purity of 95.0% (AUC).

A 12-L, round-bottom flask equipped with a mechanical stirrer, a thermocouple attached to a temperature controller, and a pH probe attached to a pH meter was charged with 10 diHCl salt (620 g, 1 wt) followed by an aqueous solution of 1 M NaOH (10 vol). The mixture was heated to 40° C., stirred until all the solids dissolved (2 h), and then transferred to a 10-L carboy. The 12-L, round-bottom flask was washed with water and then 85% phosphoric acid (124 ml, 0.2 vol) and water (1.3 vol) were charged to the reactor. The pH was adjusted to 6.5 using 50% NaOH (0.24 vol) and then heated to 65° C. The product solution in the carboy was transferred via peristaltic pump to the pH buffered solution and the pH was maintained between 6 and 7 through the addition of an aqueous solution of 6 M $HC_{1-39}$ (0.67 L). Once the addition was complete, the slurry was heated at 65° C. for 3 h and the solids were filtered. The cake was washed with water (3×5 vol) and then dried in a vacuum oven at 55° C. for 41 h to afford 473 g of 10 as a light yellow solid (87% yield) with a purity of 97.7% (AUC).

All of the publications (e.g., patents and patent applications) disclosed above are incorporated herein by reference in their entireties.

What is claimed is:

1. A method of preparing a compound of formula I(a):

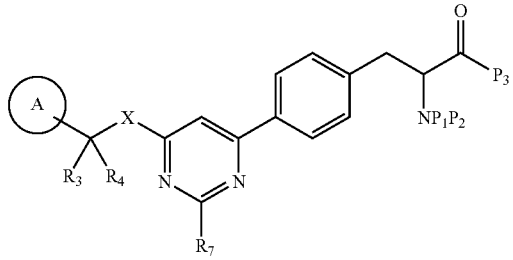

which comprises contacting a compound of formula II:

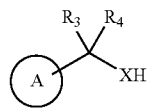

with a compound of formula III:

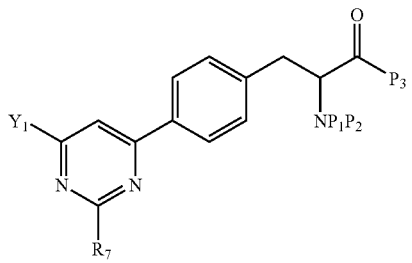

under conditions sufficient for the formation of the compound of formula I(a), wherein:

A is optionally substituted cycloalkyl, aryl, or heterocycle;
X is O, S, or $NR_6$;
$Y_1$ is halogen;
$P_1$ is $R_1$ or a protecting group;
$P_2$ is a protecting group;
$P_3$ is $OR_2$, $SR_2$, $NR_9R_{10}$, or $NHNHR_9$;
$R_1$ is hydrogen or optionally substituted alkyl, alkyl-aryl, alkyl-heterocycle, aryl, or heterocycle;
$R_2$ is hydrogen or optionally substituted alkyl, alkyl-aryl, alkyl-heterocycle, aryl, or heterocycle;
$R_3$ is hydrogen, cyano, or optionally substituted alkyl or aryl;
$R_4$ is hydrogen, cyano, or optionally substituted alkyl or aryl;
$R_6$ is hydrogen or optionally substituted alkyl or aryl;
$R_7$ is independently hydrogen, cyano, nitro, halogen, $OR_8$, $NR_9R_{10}$, or optionally substituted alkyl, alkyl-aryl or alkyl-heterocycle;
each $R_8$ is independently hydrogen or optionally substituted alkyl, alkyl-aryl or alkyl-heterocycle;
each $R_9$ is independently hydrogen, a protecting group, or optionally substituted alkyl, alkyl-aryl or alkyl-heterocycle;
each $R_{10}$ is independently hydrogen, a protecting group, or optionally substituted alkyl, alkyl-aryl or alkyl-heterocycle; and
n is 1-4.

2. The method of claim 1, wherein the compound of formula II is of formula II(a):

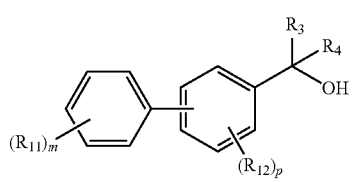

wherein:
each $R_{11}$ is independently hydrogen, cyano, nitro, halogen, $OR_8$, $NR_9R_{10}$, or optionally substituted alkyl, alkyl-aryl or alkyl-heterocycle;
each $R_{12}$ is independently hydrogen, cyano, nitro, halogen, $OR_8$, $NR_9R_{10}$, or optionally substituted alkyl, alkyl-aryl or alkyl-heterocycle;
m is 1-5; and
p is 1-4.

3. The method of claim 2, wherein the compound of formula II(a) is of formula II(b):

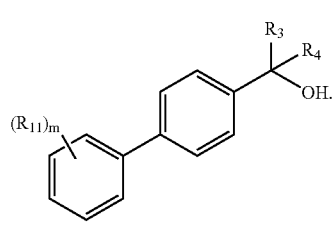

4. The method of claim 1, which further comprises deprotecting the compound of formula I(a) to provide a compound of formula I:

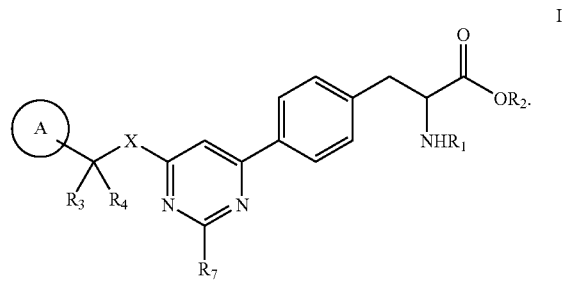

5. The method of claim 4, wherein the compound of formula I is of formula I(b):

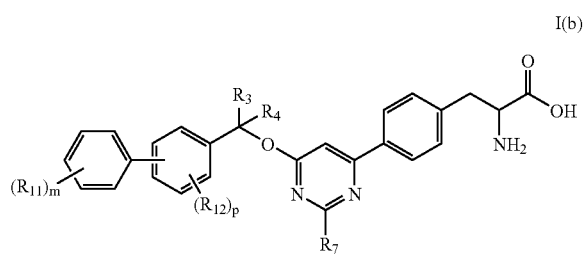

wherein:
each $R_{11}$ is independently hydrogen, cyano, nitro, halogen, $OR_8$, $NR_9R_{10}$, or optionally substituted alkyl, alkyl-aryl or alkyl-heterocycle;
each $R_{12}$ is independently hydrogen, cyano, nitro, halogen, $OR_8$, $NR_9R_{10}$, or optionally substituted alkyl, alkyl-aryl or alkyl-heterocycle;
m is 1-5; and
p is 1-4.

6. The method of claim 5, wherein the compound of formula I(b) is of formula I(c):

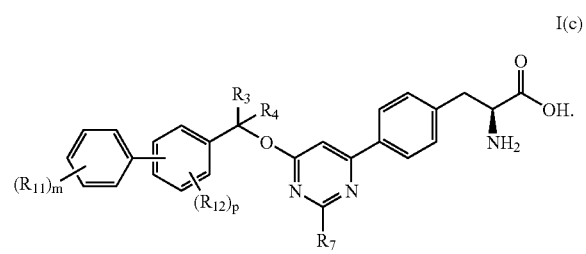

7. The method of claim 6, wherein the compound of formula I(c) is of formula I(d):

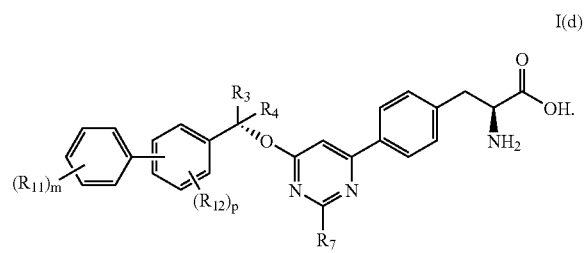

8. The method of claim 6, wherein the compound of formula I(d) is of formula I(e):

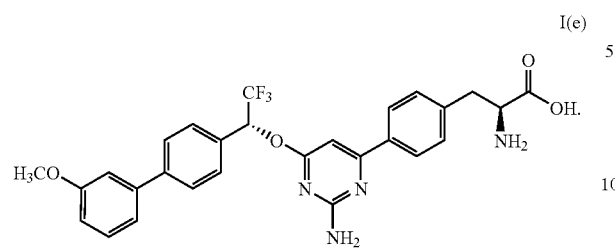

I(e)

9. A compound of the formula:

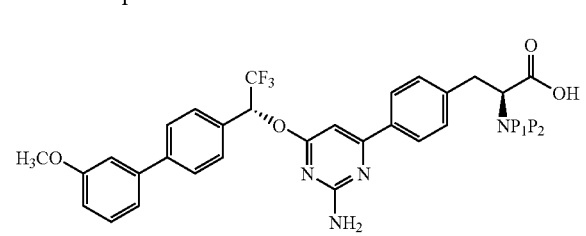

or a salt or solvate thereof, wherein:

$P_1$ is $R_1$, aryl-alkyl, heteroaryl-alkyl, or —C(O)$R_{13}$;

$P_2$ is aryl-alkyl, heteroaryl-alkyl, or —C(O)$R_{13}$;

$R_1$ is hydrogen or optionally substituted alkyl, alkyl-aryl, alkyl-heterocycle, aryl, or heterocycle; and each $R_{13}$ is independently alkyl, aryl-alkyl, aryl, heterocycle, alkoxy, aryloxy, or aryl-alkoxy.

10. The compound of claim 9, which is of the formula:

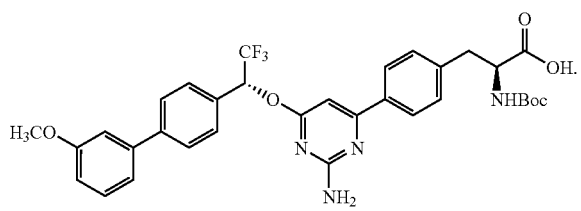

* * * * *